(12) United States Patent
Roth et al.

(10) Patent No.: US 8,765,959 B2
(45) Date of Patent: *Jul. 1, 2014

(54) PIPERIDINE DERIVATIVES

(71) Applicants: Gerald Juergen Roth, Biberach an der Riss (DE); Martin Fleck, Warthausen (DE); Bernd Nosse, Biberach an der Riss (DE); Thorsten Lehmann-Lintz, Ochsenhausen (DE)

(72) Inventors: Gerald Juergen Roth, Biberach an der Riss (DE); Martin Fleck, Warthausen (DE); Bernd Nosse, Biberach an der Riss (DE); Thorsten Lehmann-Lintz, Ochsenhausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/714,515

(22) Filed: Dec. 14, 2012

(65) Prior Publication Data
US 2013/0165444 A1     Jun. 27, 2013

(30) Foreign Application Priority Data
Dec. 23, 2011    (EP) ..................... 11195652

(51) Int. Cl.
*A61K 31/445*    (2006.01)
*C07D 211/00*    (2006.01)

(52) U.S. Cl.
USPC .......................................... 546/184; 514/317

(58) Field of Classification Search
None
See application file for complete search history.

(56) References Cited

U.S. PATENT DOCUMENTS

2012/0157425 A1    6/2012   Roth et al.

FOREIGN PATENT DOCUMENTS

| WO | 2009082346 A1 | 7/2009 |
| WO | 2011067306 A1 | 6/2011 |
| WO | 2012001107 A1 | 1/2012 |
| WO | 2012108478 A1 | 8/2012 |

OTHER PUBLICATIONS

International Search Report, PCT/ISA/210, and Written Opinion, PCT/ISA/237, for corresponding application PCT/EP2012/076592, date of mailing May 31, 2013.
Abstract in English for WO2012108478, 2012.

*Primary Examiner* — Heidi Reese
(74) *Attorney, Agent, or Firm* — Michael P. Morris; Alan R. Stempel

(57) ABSTRACT

Piperidine derivatives of which the following is exemplary

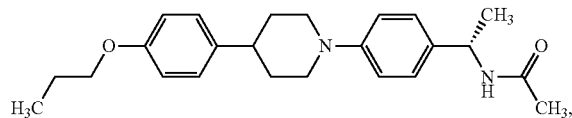

and their use in the treatment of obesity, diabetes or dyslipidemia.

16 Claims, No Drawings

PIPERIDINE DERIVATIVES

FIELD OF THE INVENTION

This invention relates to new compounds, in particular piperidine derivatives, to processes for preparing such compounds, to their use as inhibitors of acetyl-CoA carboxylase(s), to methods for their therapeutic use, in particular in diseases and conditions mediated by the inhibition of acetyl-CoA carboxylase(s), and to pharmaceutical compositions comprising them.

BACKGROUND OF THE INVENTION

Obesity is a major public health issue not only for the EU, USA, Japan but also for the world in general. It is associated with a number of serious diseases including diabetes, dyslipidemia, hypertension, cardiovascular and cerebrovascular diseases. Although the underlying mechanisms are not yet fully understood, the impairment of insulin action in target tissues by accumulation of excess lipids is generally regarded as a key mechanism linking obesity to secondary pathologies (G. Wolf, Nutrition Reviews Vol. 66(10):597-600; D B Savage, K F Petersen, G I Shulman, Physiol Rev. 2007; 87:507-520). Therefore, understanding of cellular lipid metabolism in insulin target tissues is crucial in order to elucidate the development of diseases associated with obesity.

A central event in lipid metabolism is the generation of malonyl-CoA via carboxylation of acetyl-CoA by the two mammalian ACC isoforms ACC1 (ACC-alpha, also termed ACCA) and ACC2 (ACC-beta, also designated ACCB) (Saggerson D. Annu Rev Nutr. 2008; 28:253-72). The malonyl-CoA generated is used for de novo fatty acid synthesis and acts as inhibitor of CPT-1, thereby regulating mitochondrial fatty acid oxidation. Furthermore, malonyl-CoA is also described to act centrally to control food intake, and may play an important role in controlling insulin secretion from the pancreas (G D Lopaschuk, J R Ussher, J S Jaswal. Pharmacol Rev. 2010; 62(2):237-64; D Saggerson Annu Rev Nutr. 2008; 28:253-72), further coordinating the regulation of intermediary metabolism.

Therefore ACC1 and ACC2 have been shown to be major regulators of fatty acid metabolism and are presently considered as an attractive target to regulate the human diseases of obesity, diabetes and cardiovascular complications (S J Wakil and L A Abu-Elheiga, J. Lipid Res. 2009. 50: S138-S143; L. Tong, H J Harwood Jr. Journal of Cellular Biochemistry 99:1476-1488, 2006).

As a result of its unique position in intermediary metabolism, inhibition of ACC offers the ability to inhibit de novo fatty acid production in lipogenic tissues (liver and adipose) while at the same time stimulating fatty acid oxidation in oxidative tissues (liver, heart, and skeletal muscle) and therefore offers an attractive modality for favorably affecting, in a concerted manner, a multitude of cardiovascular risk factors associated with obesity, diabetes, insulin resistance, nonalcoholic steatohepatitis (NASH) and the metabolic syndrome (L. Tong, H J Harwood Jr. Journal of Cellular Biochemistry 99:1476-1488, 2006; Corbett J W, Harwood J H Jr., Recent Pat Cardiovasc Drug Discov. 2007 November; 2(3):162-80).

Furthermore recent data show that cellular toxicity mediated by lipids (lipotoxicity) is implicated in the susceptibitlity to diabetes associated nephropathy (for review see M Murea, B I Freedmann, J S Parks, P A Antinozzi, S C Elbein, L M Ma; Clin J Am Soc Nephrol. 2010; 5:2373-9). A large-scale genome-wide association study in japanese patients identified single nucleotide polymorphism in the ACC2 gene (ACACB) associated with diabetic nephropathy risk which was replicated in nine independent cohorts. In the kidney, dysregulation of fatty acid metabolism leading to increased fatty acid levels is believed to lead to glomerular and tubular dysfunction (M Murea, B I Freedmann, J S Parks, P A Antinozzi, S C Elbein, L M Ma; Clin J Am Soc Nephrol. 2010; 5:2373-9). Therefore inhibitors targeting ACC as key molecule involved in lipid oxidation have the potential to be beneficial for favorably affecting diabetic nephropathy.

Additionally, insulin resistance, deregulated lipid metabolism, lipotoxicity and increased intramuscular lipids have also been described to play a role in type 1 diabetes (I E Schauer, J K Snell-Bergeon, B C Bergman, D M Maahs, A Kretowski, R H Eckel, M Rewers Diabetes 2011; 60:306-14; P Ebeling, B Essen-Gustaysson, J A Tuominen and V A Koivisto Diabetologia 41: 111-115; K J Nadeau, J G Regensteiner, T A Bauer, M S Brown, J L Dorosz, A Hull, P Zeitler, B Draznin, JEB. Reusch J Clin Endocrinol Metab, 2010, 95:513-521). Therefore ACC inhibitors are also considered as interesting drugs for the treatment of type 1 diabetes.

In addition ACC inhibitors also have the potential to intervene in the progression of diseases that result from the rapid growth of malignant cells or invading organisms that are dependent on endogenous lipid synthesis to sustain their rapid proliferation. De novo lipogenesis is known to be required for growth of many tumor cells and ACC up-regulation has been recognized in multiple human cancers, promoting lipogenesis to meet the need of cancer cells for rapid growth and proliferation (C Wang, S Rajput, K Watabe, D F Liao, D Cao Front Biosci 2010; 2:515-26). This is further demonstrated in studies using ACC inhibitors which induced growth arrest and selective cytotoxicity in cancer cells and by RNA interference-mediated knock-down of ACC which inhibited growth and induced apoptosis in different types of cancer cells. Furthermore, ACC1 associates with and is regulated by the breast cancer susceptibility gene 1 (BRCA1). Commonly occurring BRCA1 mutations lead to ACC1 activation and breast cancer susceptibility (C Wang, S Rajput, K Watabe, D F Liao, D Cao Front Biosci 2010; 2:515-26).

Furthermore in central nervous system disorders including but not limited to Alzheimer's disease, Parkinson disease and epilepsy, impairements in neuronal energy metabolism have been described (Ogawa M, Fukuyama H, Ouchi Y, Yamauchi H, Kimura J, J Neurol Sci. 1996; 139(1):78-82). Interventions targeting this metabolic defect may prove beneficial to the patients. One promising intervention is therefore to provide the glucose-compromised neuronscerebral brain neurons with ketone bodies as an alternative substrate (S T Henderson Neurotherapeutics, 2008, 5:470-480; L C Costantini, L J Barr, J L Vogel, S T Henderson BMC Neurosci. 2008, 9 Suppl 2:S16; K W Baranano, A L Hartman. Curr Treat Options Neurol. 2008; 10:410-9). ACC inhibition leading to increased fatty acid oxidation may thereby result in increases in the blood levels of ketone bodies thereby providing an alternative energy substrate for the brain.

Preclinical and clinical evidence indicates that ketone bodies can provide neuroprotective effects in models of Parkinson's disease, AD, hypoxia, ischemia, amyotrophic lateral sclerosis and glioma (L C Costantini, L J Barr, J L Vogel, S T Henderson BMC Neurosci. 2008, 9 Suppl 2:S16) and improved cognitive scores in Alzheimers Diseases patients (M A Reger, S T Henderson, C Hale, B Cholerton, L D Baker, G S Watson, K Hydea, D Chapmana, S Craft Neurobiology of Aging 25 (2004) 311-314). The end result of increased ketone levels is an improvement in mitochondrial efficiency and reduction in the generation of reactive oxygen species (for reviews see L C Costantini, L J Barr, J L Vogel, S T Henderson BMC Neurosci. 2008, 9 Suppl 2:S16; K W Barañano, A L Hartman. Curr Treat Options Neurol. 2008; 10:410-9).

Furthermore, the potential of ACC inhibitors as antifungal agents and as antibacterial agents is well documented (L. Tong, H J Harwood Jr. Journal of Cellular Biochemistry 99:1476-1488, 2006). In addition, ACC inhibitors can be used to combat viral infections. It was discovered recently that viruses rely on the metabolic network of their cellular hosts to provide energy and building blocks for viral replication (Munger J, B D Bennett, A Parikh, X J Feng, J McArdle, H A Rabitz, T Shenk, J D Rabinowitz. *Nat. Biotechnol.* 2008; 26:1179-86). A flux measurement approach to quantify changes in metabolic activity induced by human cytomegalovirus (HCMV) elucidated that infection with HCMV markedly changed fluxes through much of the central carbon metabolism, including glycolysis, tricarboxylic acid cycle and fatty acid biosynthesis. Pharmacological inhibition of fatty acid biosynthesis suppressed the replication of two divergent enveloped viruses (HCMV and influenza A) indicating that fatty acid synthesis is essential for the replication. These examples show that acetyl-CoA fluxes and de novo fatty acid biosynthesis are critical to viral survival and propagation as the newly synthesized fatty acids and phospholipids are important for formation of viral envelopes. Changing the metabolic flux influences the absolute quantity of phospholipid available, the chemical composition and physical properties of the envelope negatively affect viral growth and replication. Hence, ACC inhibitors acting on key enzymes in the fatty acid metabolism, have the potential to be antiviral drugs.

AIM OF THE PRESENT INVENTION

The aim of the present invention is to provide new compounds, in particular new piperidine derivatives, which are active with regard to acetyl-CoA carboxylase(s).

Another aim of the present invention is to provide new compounds, in particular new piperidine derivatives, which are active with regard to ACC2.

A further aim of the present invention is to provide new compounds, in particular new piperidine derivatives, which have an inhibitory effect on acetyl-CoA carboxylase(s) in vitro and/or in vivo and possess suitable pharmacological and pharmacokinetic properties to use them as medicaments.

A further aim of the present invention is to provide new compounds, in particular new piperidine derivatives, which have an inhibitory effect on ACC2 in vitro and/or in vivo and possess suitable pharmacological and pharmacokinetic properties to use them as medicaments.

A further aim of the present invention is to provide effective ACC inhibitors, in particular for the treatment of metabolic disorders, for example of obesity and/or diabetes.

A further aim of the present invention is to provide methods for treating a disease or condition mediated by the inhibition of acetyl-CoA carboxylase(s) in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular piperidine derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

Within the scope of the present invention it has now surprisingly been found that the new compounds of general formula (I) as described hereinafter exhibit an inhibiting activity with regard to acetyl-CoA carboxylase(s).

According to another aspect of the present invention it has been found that the new compounds of general formula (I) as described hereinafter exhibit an inhibiting activity with regard to ACC2.

In a first aspect the present invention provides a compound of general formula (I)

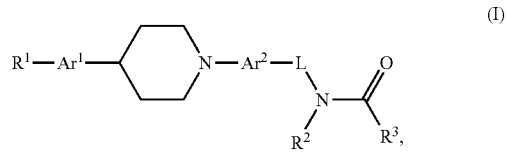

(I)

wherein
Ar$^1$ is selected from the group Ar$^1$-G1 consisting of:
  6- to 10 membered arylene and 5- to 10-membered heteroarylene all of which may be optionally substituted with one or more substituents R$^A$, wherein R$^1$ and R$^A$ linked to adjacent C-atoms of Ar$^1$ may be connected with each other and together form a C$_{3-5}$-alkylene bridging group in which 1, 2 or 3-CH$_2$-groups may be replaced by O, C(=O), S, S(=O), S(=O)$_2$, NH or N(C$_{1-4}$-alkyl)-, wherein the alkylene bridge may optionally be substituted by one or two C$_{1-3}$-alkyl groups;
R$^A$ is selected from the group R$^A$-G1 consisting of:
  H, F, Cl, Br, I, CN, OH, —NO$_2$, C$_{1-4}$-alkyl, C$_{2-4}$-alkenyl, C$_{1-4}$-alkyl-O—, C$_{3-7}$-cycloalkyl-O—, C$_{1-4}$-alkyl-C(=O)—, H$_2$N—, H$_2$N—C(=O)—, H$_2$N—S(=O)$_2$—, HO—C(=O)—, C$_{1-4}$-alkyl-O—C(=O)—, phenyl and phenyl-C$_{1-3}$-alkyl,
    wherein in each NH$_2$-group, one or both hydrogen atoms may independently be replaced by C$_{1-4}$-alkyl;
    wherein each alkyl or cycloalkyl may be optionally substituted with one or more substituents selected from F and OH;
Ar$^2$ is selected from the group Ar$^2$-G1 consisting of:
  phenylene and a 5- or 6-membered monocyclic aromatic ring containing 1, 2 or 3 heteroatoms selected from N, O, or S,
    wherein all of the before mentioned groups may be optionally substituted with one or more substituents R$^A$;
L is selected from the group L-G1 consisting of:
  straight-chain C$_{1-4}$-alkylene, which may optionally be substituted with one or two C$_{1-3}$-alkyl groups;
R$^1$ is selected from the group R$^1$-G1 consisting of:
  OH, C$_{1-4}$-alkyl-O—, C$_{3-7}$-cycloalkyl-O—, H$_2$N—, (C$_{1-4}$-alkyl)NH—, (C$_{1-4}$-alkyl)$_2$N—, C$_{3-7}$-cycloalkyl-NH—, C$_{3-7}$-cycloalkyl-C$_{1-3}$-alkyl-NH—, C$_{1-4}$-alkyl-C(=O)—, C$_{1-4}$-alkyl-S(=O)$_2$—, HO—C(=O)—, C$_{1-4}$-alkyl-O—C(=O)—, H$_2$N—C(=O)—, (C$_{1-4}$-alkyl)HN—C(=O)—, heterocyclyl-O—, heterocyclyl-C$_{1-3}$-alkyl-O—, aryl-O—, aryl-C$_{1-3}$-alkyl-O—, and (C$_{1-4}$-alkyl)$_2$N—C(=O)—, wherein each alkyl or cycloalkyl may be optionally substituted with one or more substituents selected from F and OH;

$R^2$ is selected from the group $R^2$-G1 consisting of: H and $C_{1-3}$-alkyl; and $R^3$ is selected from the group $R^3$-G1 consisting of:
  H, $C_{1-6}$-alkyl, —O—($C_{1-4}$-alkyl), $C_{3-10}$-carbocyclyl, $C_{3-10}$-carbocyclyl-$C_{1-3}$-alkyl, $C_{2-6}$-alkenyl, $C_{2-6}$-alkinyl, $R^{N1}R^{N2}N$—, heterocyclyl, heterocyclyl-$C_{1-3}$-alkyl, aryl, aryl-$C_{1-3}$-alkyl, heteroaryl and heteroaryl-$C_{1-3}$-alkyl,
    wherein each aryl, heteroaryl, carbocyclyl and heterocyclyl may be optionally substituted with one or more $C_{1-4}$-alkyl, and
    wherein in each carbocyclyl and heterocyclyl a —$CH_2$- group may optionally be replaced by —C(=O)—, and
    wherein each alkyl, carbocyclyl, heterocyclyl, aryl and heteroaryl group may be optionally substituted with one or more substituents $R^4$; wherein $R^4$ is selected from the group $R^4$-G1 consisting of:
  F, Cl, Br, CN, OH, $O_{1-4}$-alkyl, —O—($C_{1-4}$-alkyl), —S—($C_{1-4}$-alkyl), and —NH—C(=O)—$C_{1-3}$-alkyl;

$R^{N1}$ is selected from the group $R^{N1}$-G1 consisting of:
  H and $C_{1-3}$-alkyl; and $R^{N2}$ is selected from the group $R^{N2}$-G1 consisting of:
  H, $C_{1-3}$-alkyl, $O_{3-10}$-carbocyclyl, $C_{3-10}$-carbocyclyl-$C_{1-3}$-alkyl, $C_{3-6}$-alkenyl, $C_{3-6}$-alkynyl, heterocyclyl, heterocyclyl-$C_{1-3}$-alkyl, aryl, aryl-$C_{1-3}$-alkyl, heteroaryl and heteroaryl-$C_{1-3}$-alkyl,
    wherein each carbocyclyl and heterocyclyl may be optionally substituted with one or more $C_{1-4}$-alkyl, aryl or aryl-$C_{1-3}$-alkyl-, and
    wherein in each carbocyclyl and heterocyclyl a $CH_2$-group may optionally be replaced by —C(=O)—; and
    wherein each alkyl or cycloalkyl may be optionally substituted with one or more substituents selected from F and OH; and
    with the provision that there is at least one $CH_2$-group between any double or triple bond of the alkenyl and alkynyl groups and the nitrogen atom to which they are attached;

including any tautomers and stereoisomers thereof,
or a salt thereof
or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of acetyl-CoA carboxylase(s) in a patient in need thereof characterized in that a compound of general formula (I) or a pharmaceutically acceptable salt thereof is administered to the patient.

According to another aspect of the invention, there is provided a method for treating a metabolic disease or disorder in a patient in need thereof characterized in that a compound of general formula (I) or a pharmaceutically acceptable salt thereof is administered to the patient.

According to another aspect of the invention, there is provided a method for treating a cardiovascular disease or disorder in a patient in need thereof characterized in that a compound of general formula (I) or a pharmaceutically acceptable salt thereof is administered to the patient.

According to another aspect of the invention, there is provided a method for treating a neurodegenerative disease or disorder or for treating a disease or disorder of the central nervous system in a patient in need thereof characterized in that a compound of general formula (I) or a pharmaceutically acceptable salt thereof is administered to the patient.

According to another aspect of the invention, there is provided a method for treating a cancer, a malignant disorder or a neoplasia in a patient in need thereof characterized in that a compound of general formula (I) or a pharmaceutically acceptable salt thereof is administered to the patient.

According to another aspect of the invention, there is provided the use of a compound of the general formula (I) or a pharmaceutically acceptable salt thereof for the manufacture of a medicament for a therapeutic method as described hereinbefore and hereinafter.

According to another aspect of the invention, there is provided a compound of the general formula (I) or a pharmaceutically acceptable salt thereof for a therapeutic method as described hereinbefore and hereinafter.

In a further aspect this invention relates to a method for treating a disease or condition mediated by the inhibition of acetyl-CoA carboxylase(s) in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) or a pharmaceutically acceptable salt thereof in combination with one or more additional therapeutic agents for the treatment or prevention of diseases or conditions which are mediated by the inhibition of acetyl-CoA carboxylase(s).

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $Ar^1$, $Ar^2$, $R^1$, $R^2$, $R^3$ and L, are defined as above and hereinafter. If residues, substituents, or groups occur several times in a compound, as for example $R^4$, $R^{N1}$, $R^{N2}$ or $R^4$, they may have the same or different meanings. Some preferred meanings of individual groups and substituents of the compounds according to the invention will be given hereinafter. Any and each of these definitions may be combined with each other.

$Ar^1$:

$Ar^1$-G1:

The group $Ar^1$ is preferably selected from the group $Ar^1$-G1 as defined hereinbefore and hereinafter.

$Ar^1$-G2:

In one embodiment the group $Ar^1$ is selected from the group $Ar^1$-G2 consisting of: phenylene, naphthylene, pyridylene, 2H-pyridin-2-onylene, pyrimidinylene, pyridazinylene, pyrazinylene, quinolinylene, indan-1-onylene, benzo[1,3]dioxolylene, 2,3-dihydro-benzo[1,4]dioxinylene and 3,4-dihydro-2H-benzo[b][1,4]dioxepinylene,
  wherein the before mentioned bicyclic groups preferably are linked to the ring of the core structure of the formula (I) via an aromatic or heteroaromatic ring of the bicyclic group, and
  wherein all of the before mentioned groups may be optionally substituted with one or more substituents $R^4$.

$Ar^1$-G3:
  In another embodiment the group $Ar^1$ is selected from the group $Ar^1$-G3 consisting of: phenylene and pyridinylene,
    wherein each of the beforementioned groups may be substituted with a substituent $R^4$.

$Ar^1$-G3a:
  In another embodiment the group $Ar^1$ is selected from the group $Ar^1$-G3a consisting of: phenylene, which may be substituted with $R^4$.

$Ar^1$-G4:
  In another embodiment the group $Ar^1$ is selected from the group $Ar^1$-G4 consisting of:

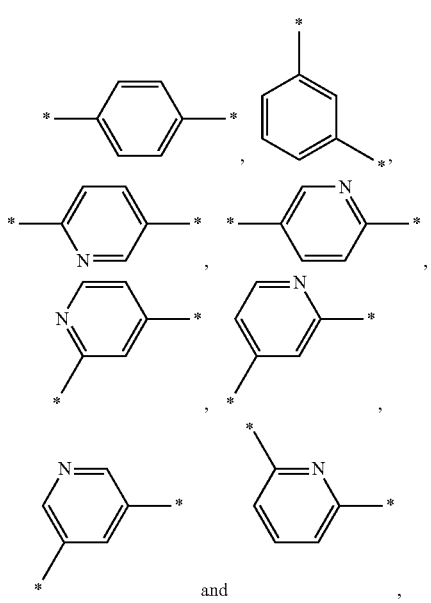

wherein the asterisk to the right side of each group indicates the bond which is connected to the piperidine ring of the core structure of the formula (I), and the asterisk to the left side of each group indicates the bond which is connected to a substituent $R^1$, and in addition each of the before mentioned groups is optionally substituted with a substituent $R^4$.

$Ar^1$-G4a:
  In another embodiment the group $Ar^1$ is selected from the group $Ar^1$-G4a consisting of:

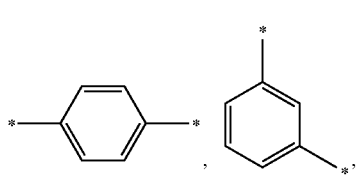

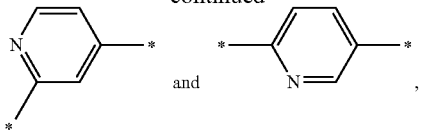

wherein the asterisk to the right side of each group indicates the bond which is connected to the piperidine ring of the core structure of the formula (I), and the asterisk to the left side of each group indicates the bond which is connected to a substituent $R^1$, and in addition each of the before mentioned phenyl groups is optionally substituted with F, —$CH_3$ or —$OCH_3$.

$Ar^1$-G4b:
  In another embodiment the group $Ar^1$ is selected from the group $Ar^1$-G4b consisting of:

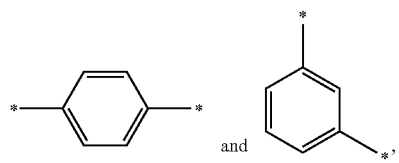

wherein the beforementioned 1,4-phenylene group is optionally substituted with F, —$CH_3$ or —$OCH_3$.

$Ar^1$-G5:
  In another embodiment the group $Ar^1$ is selected from the group $Ar^1$-G5 consisting of:

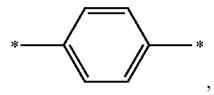

wherein the before mentioned group is optionally substituted with F, —$CH_3$ or —$OCH_3$ $Ar^1$-G5a:
  In another embodiment the group $Ar^1$ is selected from the group $Ar^1$-G5a consisting of:

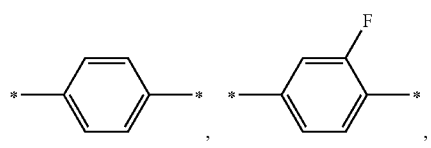

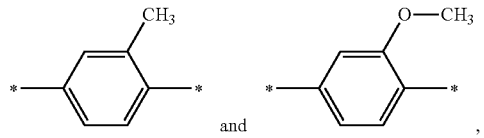

wherein the asterisk to the right side of the cyclic group indicates the bond which is connected to the piperidine ring of the core structure of the formula (I), and the asterisk to the left side of the cyclic group indicates the bond which is connected to a substituent $R^1$.

$Ar^1$-G6:

In another embodiment the group $Ar^1$ is selected from the group $Ar^1$-G6 consisting of:

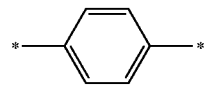

$R^A$:

$R^A$-G1:

The group $R^A$ is preferably selected from the group $R^A$-G1 as defined hereinbefore and hereinafter.

$R^A$-G2:

In another embodiment the group $R^A$ is selected from the group $R^A$-G2 consisting of: H, F, Cl, Br, CN, OH, —$NO_2$, $C_{1-4}$-alkyl, $C_{1-4}$-alkyl-O—, $H_2N$—, $C_{1-6}$-alkyl-O—C(=O)—, phenyl and phenyl-$CH_2$—, wherein in each $NH_2$-group, one or both hydrogen atoms may independently be replaced by $O_{1-4}$-alkyl.

$R^A$-G3:

In another embodiment the group $R^A$ is selected from the group $R^A$-G3 consisting of:

H, F, Cl, CN, OH, $C_{1-3}$-alkyl and $C_{1-3}$-alkyl-O—.

$R^A$-G4:

In another embodiment the group $R^A$ is selected from the group $R^A$-G4 consisting of: H, F, —$CH_3$ and —$OCH_3$.

$R^A$-G5:

In another embodiment the group $R^A$ is selected from the group $R^A$-G5 consisting of: H, —$CH_3$ and —$OCH_3$.

$Ar^2$:

$Ar^2$-G1:

The group $Ar^2$ is preferably selected from the group $Ar^2$-G1 as defined hereinbefore and hereinafter.

$Ar^2$-G2:

In another embodiment the group $Ar^2$ is selected from the group $Ar^2$-G2 consisting of: phenylene, which may be optionally substituted with one or two substituents $R^A$.

$Ar^2$-G2a:

In another embodiment the group $Ar^2$ is selected from the group $Ar^2$-G2a consisting of: phenylene, which may be optionally substituted with F or —$OCH_3$.

$Ar^2$-G2b:

In another embodiment the group $Ar^2$ is selected from the group $Ar^2$-G2b consisting of: phenylene, which may be optionally substituted with one F.

$Ar^2$-G3:

In another embodiment the group $Ar^2$ is selected from the group $Ar^2$-G3 consisting of:

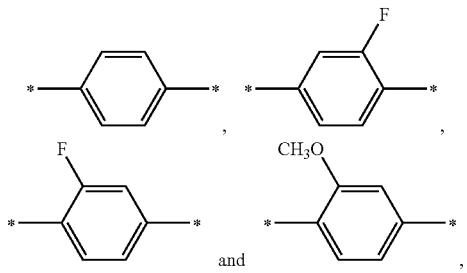

wherein the asterisk to the left side of each group indicates the bond which is connected to the piperidine ring of the core structure of the formula (I), and the asterisk to the right side of each group indicates the bond which is connected to L.

$Ar^2$-G3a:

In another embodiment the group $Ar^2$ is selected from the group $Ar^2$-G3a consisting of:

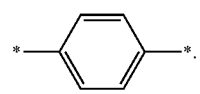

L:

L-G1:

The group L is preferably selected from the group L-G1 as defined hereinbefore and hereinafter.

L-G2:

In another embodiment the group L is selected from the group L-G2 consisting of: straight-chain $C_{1-4}$-alkylene, which may optionally be substituted with one or two methyl groups.

L-G3:

In another embodiment the group L is selected from the group L-G3 consisting of: straight-chain $C_{1-3}$-alkylene, which may optionally be substituted with one or two methyl groups.

L-G3a:

In another embodiment the group L is selected from the group L-G3a consisting of: straight-chain $C_{1-3}$-alkylene, which may optionally be substituted with one methyl group.

L-G4:

In another embodiment the group L is selected from the group L-G4 consisting of:

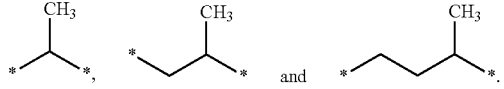

L-G4a:

In another embodiment the group L is selected from the group L-G4a consisting of:

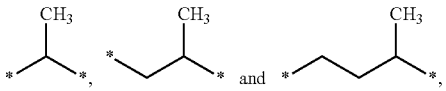

wherein the right-hand side of each of the before-mentioned moieties is attached to the N atom in formula (I) and the left-hand side of each of the before-mentioned moieties is attached to the $Ar^2$ group.

L-G5:

In another embodiment the group L is selected from the group L-G5 consisting of —$CH(CH_3)$—.

L-G5a:

According to another embodiment, the group L is selected from the group L-G5a consisting of:

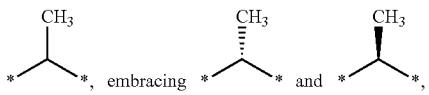

wherein the right-hand side of each of the before-mentioned moieties is attached to the N atom in formula (I) and the left-hand side of each of the before-mentioned moieties is attached to the $Ar^2$ group.

A preferred example of the group L-G5a is

wherein the right-hand side of the before-mentioned moiety is attached to the N atom in formula (I) and the left-hand side of the before-mentioned moiety is attached to the $Ar^2$ group.

Another preferred example of the group L-G5a is

wherein the right-hand side of the before-mentioned moiety is attached to the N atom in formula (I) and the left-hand side of the before-mentioned moiety is attached to the $Ar^2$ group.

$R^1$ $R^1$-G1:

The group $R^1$ is preferably selected from the group $R^1$-G1 as defined hereinbefore and hereinafter.

$R^1$-G2:

In another embodiment the group $R^1$ is selected from the group $R^1$-G2 consisting of: OH, $C_{1-4}$-alkyl-O—, $C_{3-7}$-cycloalkyl-O—, $H_2N$—, $(C_{1-4}$-alkyl)NH—, $(C_{1-4}$-alkyl$)_2$N—, $C_{3-7}$-cycloalkyl-NH— and $C_{3-7}$-cycloalkyl-N($C_{1-4}$-alkyl)-,
  wherein each alkyl or cycloalkyl may be optionally substituted with one or more substituents selected from F and OH.

$R^1$-G3:

In another embodiment the group $R^1$ is selected from the group $R^1$-G3 consisting of: $C_{1-4}$-alkyl-O—, $C_{3-6}$-cycloalkyl-O—, $C_{3-6}$-cycloalkyl-$C_{1-3}$-alkyl-O—, $H_2N$—, $(C_{1-4}$-alkyl)NH—, $(C_{1-3}$-alkyl$)_2$N—, $C_{3-6}$-cycloalkyl-NH— and $C_{3-7}$-cycloalkyl-N($C_{1-4}$-alkyl)-,
  wherein each alkyl or cycloalkyl may be optionally substituted with one or more F atoms.

$R^1$-G4:

In another embodiment the group $R^1$ is selected from the group $R^1$-G4 consisting of: $C_{1-4}$-alkyl-O—, $C_{3-6}$-cycloalkyl-O— and $C_{3-6}$-cycloalkyl-$C_{1-3}$-alkyl-O—,
  wherein each alkyl and cycloalkyl may be optionally substituted with one or more F atoms.

$R^1$-G4a:

In another embodiment the group $R^1$ is selected from the group $R^1$-G4a consisting of: $C_{1-4}$-alkyl-O—, $C_{3-6}$-cycloalkyl-O— and $C_{3-6}$-cycloalkyl-$CH_2$—O—,
  wherein each alkyl and cycloalkyl may be optionally substituted with one or two F atoms.

$R^1$-G4b:

In another embodiment the group $R^1$ is selected from the group $R^1$-G4b consisting of: $C_{1-4}$-alkyl-O—, $C_{3-6}$-cycloalkyl-O— and $C_{3-6}$-cycloalkyl-$CH_2$—O—,
  wherein each cycloalkyl may be optionally substituted with one or two F atoms.

$R^1$-G5:

In another embodiment the group $R^1$ is selected from the group $R^1$-G5 consisting of: $C_{1-4}$-alkyl-O—, $C_{3-4}$-cycloalkyl-O— and $C_{3-4}$-cycloalkyl-$CH_2$—O—,
  wherein each alkyl and cycloalkyl may be optionally substituted with one or two F atoms.

$R^1$-G5a:

In another embodiment the group $R^1$ is selected from the group $R^1$-G5a consisting of: $C_{1-4}$-alkyl-O—, $C_{3-4}$-cycloalkyl-O— and $C_{3-4}$-cycloalkyl-$CH_2$—O—,
  wherein each cycloalkyl may be optionally substituted with one or two F atoms.

$R^1$-G5b:

In another embodiment the group $R^1$ is selected from the group $R^1$-G5b consisting of: $C_{1-3}$-alkyl-O—, cyclobutyl-O— and cyclopropyl-$CH_2$—O—,
  wherein the cyclopropyl group may be optionally substituted with one or preferably two F atoms.

$R^2$ $R^2$-G1:

The group $R^2$ is preferably selected from the group $R^2$-G1 as defined hereinbefore and hereinafter.

$R^2$-G2:

In another embodiment the group $R^2$ is selected from the group $R^2$-G2 consisting of: H and $CH_3$.

$R^2$-G3:

In another embodiment the group $R^2$ is selected from the group $R^2$-G3 consisting of: H.

$R^3$ $R^3$-G1:

The group $R^3$ is preferably selected from the group $R^3$-G1 as defined hereinbefore and hereinafter.

$R^3$-G2:

In another embodiment the group $R^3$ is selected from the group $R^3$-G2 consisting of: $C_{1-4}$-alkyl, —O—($C_{1-3}$-alkyl), $C_{3-7}$-cycloalkyl, $C_{3-7}$-cycloalkyl-$C_{1-3}$-alkyl, $C_{2-6}$-alkenyl, $C_{2-6}$-alkinyl, $R^{N1}R^{N2}N$—, heterocyclyl, heterocyclyl-$CH_2$—, aryl, aryl-$CH_2$—, heteroaryl and heteroaryl-$CH_2$—,
  wherein in each heterocyclyl a —$CH_2$-group may optionally be replaced by —C(=O)—, and
  wherein each alkyl, carbocyclyl, heterocyclyl, aryl and heteroaryl group may be optionally substituted with one or more substituents $R^4$; wherein
  $R^4$ is selected from the group $R^4$-G1 consisting of:
  F, Cl, Br, CN, OH, $C_{1-4}$-alkyl, —O—($C_{1-4}$-alkyl), —S—($C_{1-4}$-alkyl), and —NH—C(=O)—$C_{1-3}$-alkyl;

$R^3$-G3:

In another embodiment the group $R^3$ is selected from the group $R^3$-G3 consisting of: $C_{1-3}$-alkyl, —O—($C_{1-2}$-alkyl), $C_{3-5}$-cycloalkyl, $C_{3-5}$-cycloalkyl-$CH_2$—, $R^{N1}N^{R2}N$—, morpholinyl, heteroaryl and heteroaryl-$CH_2$—,
  wherein each alkyl may be optionally substituted with one to three F atoms and/or one CN, OH, —O—($C_{1-3}$-alkyl) and —S—$CH_3$, and
  wherein each cycloalkyl may be optionally substituted with one CN, OH, or $C_{1-3}$-alkyl, and wherein each heteroaryl group may be optionally substituted with one or more substituents independently selected from the group consisting of $C_{1-3}$-alkyl and —NH—C(=O)—$C_{1-3}$-alkyl.

$R^3$-G4:

In another embodiment the group $R^3$ is selected from the group $R^3$-G4 consisting of: $C_{1-3}$-alkyl, —O—($C_{1-2}$-alkyl), $C_{3-5}$-cycloalkyl, $R^{N1}R^{N2}N$—, morpholinyl, heteroaryl and heteroaryl-$CH_2$—, wherein each alkyl may be optionally substituted with one to three F atoms or one CN, OH, —O—$CH_3$ and —S—$CH_3$, and wherein each cycloalkyl may be optionally substituted with one CN, OH, or —$CH_3$, and wherein each heteroaryl group is selected from the group consisting of pyrrolyl, imidazolyl, pyrazolyl, oxazoly, thiazolyl, benzimidazolyl and pyridinyl, and wherein each heteroaryl group may be optionally substituted with one or more substituents independently selected from the group consisting of phenyl, —$CH_3$ and —NH—C(=O)—$CH_3$, and wherein $R^{N1}$ is selected from the group consisting of H and $C_{1-3}$-alkyl, and wherein $R^{N2}$ is selected from the group consisting of H, $C_{1-3}$-alkyl and pyridinyl.

$R^3$-G5:

In another embodiment the group $R^3$ is selected from the group $R^3$-G5 consisting of: $C_{1-3}$-alkyl, —O—$CH_3$, cyclopropyl, $R^{N1}R^{N2}N$—, morpholinyl, heteroaryl and heteroaryl-$CH_2$—, wherein each alkyl may be optionally substituted with one to three F atoms or one CN, OH, —O—$CH_3$ and —S—$CH_3$, and wherein each cycloalkyl may be optionally substituted with one CN, or —$CH_3$, and wherein each heteroaryl group is selected from the group consisting of pyrrolyl, pyrazolyl, oxazolyl, thiazolyl and pyridinyl, and wherein each heteroaryl group may be optionally substituted with one or two substituents independently selected from the group consisting of —$CH_3$ and —NH—C(=O)—$CH_3$, and wherein $R^{N1}$ is selected from the group consisting of H and $C_{1-2}$-alkyl, and, wherein $R^{N2}$ is selected from the group consisting of H, $C_{1-3}$-alkyl and pyridinyl.

$R^3$-G5a:

In another embodiment the group $R^3$ is selected from the group $R^3$-G5a consisting of: $C_{1-3}$-alkyl, —$CH_2F$, —$CHF_2$, —$CF_3$, —CHF—$CH_3$, —$CH_2$—OH, —$CH_2$—$OCH_3$, —$CH_2$—S—$CH_3$, —$OCH_3$, —N($C_{1-2}$-alkyl)$_2$,

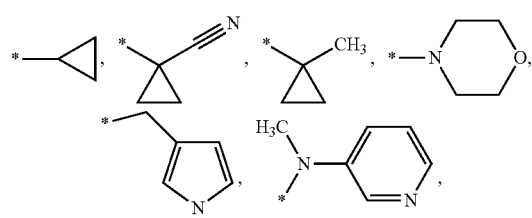

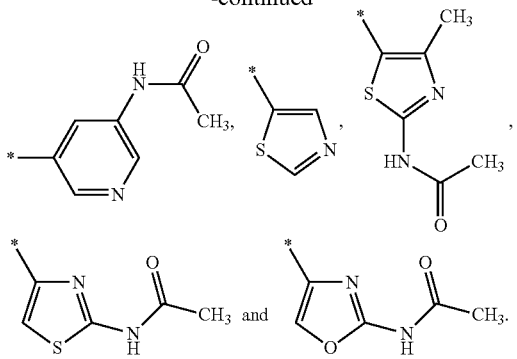

$R^3$-G6:

In another embodiment the group $R^3$ is selected from the group $R^3$-G6 consisting of: —$CH_3$, cyclopropyl and —N($CH_3$)$_2$.

$R^3$-G6a:

In another embodiment the group $R^3$ is selected from the group $R^3$-G6a consisting of: —$CH_3$ and cyclopropyl.

$R^3$-G6b:

In another embodiment the group $R^3$ is selected from the group $R^3$-G6b consisting of: —$CH_3$.

$R^4$ $R^4$-G1:

The group $R^4$ is preferably selected from the group $R^4$-G1 as defined hereinbefore and hereinafter.

$R^4$-G2:

In another embodiment the group $R^4$ is selected from the group $R^4$-G2 consisting of: F, Cl, Br, $C_{1-3}$-alkyl, —O—($C_{1-3}$-alkyl) and —NH—C(=O)—$C_{1-3}$-alkyl;

$R^4$-G3:

In another embodiment the group $R^4$ is selected from the group $R^4$-G3 consisting of: —$C_{1-3}$-alkyl and —NH—C(=O)—$C_{1-3}$-alkyl.

$R^4$-G4:

In another embodiment the group $R^4$ is selected from the group $R^4$-G4 consisting of: —$CH_3$ and —NH—C(=O)—$CH_3$.

$R^{N1}$ $R^{N1}$-G1:

The group $R^{N1}$ is preferably selected from the group $R^{N1}$-G1 as defined hereinbefore and hereinafter.

In another embodiment the group $R^{N1}$ is selected from the group $R^{N1}$-G2 consisting of: H, methyl and ethyl.

In another embodiment the group $R^{N1}$ is selected from the group $R^{N1}$-G3 consisting of: methyl.

$R^{N2}$

The group $R^{N2}$ is preferably selected from the group $R^{N2}$-G1 as defined hereinbefore and hereinafter.

$R^{N2}$-G2:

In another embodiment the group $R^{N2}$ is selected from the group $R^{N2}$-G2 consisting of: H, $C_{1-3}$-alkyl, $C_{3-7}$-cycloalkyl-, phenyl, pyridinyl and pyrimidinyl.

$R^{N2}$-G3:

In another embodiment the group $R^{N2}$ is selected from the group $R^{N2}$-G3 consisting of: H, $C_{1-3}$-alkyl and pyridinyl.

Examples of preferred subgeneric embodiments according to the present invention are set forth in the following table, wherein each substituent group of each embodiment is defined according to the definitions set forth hereinbefore and wherein all other substituents of the formula (I) are defined according to the definitions set forth hereinbefore:

| Embodiment | R¹ | Ar¹ | R⁴ | Ar² | L | R² | R³ |
|---|---|---|---|---|---|---|---|
| E-1 | R¹-G1 | Ar¹-G1 | R⁴-G1 | Ar²-G1 | L-G1 | R²-G1 | R³-G1 |
| E-2 | R¹-G2 | Ar¹-G2 | R⁴-G2 | Ar²-G1 | L-G2 | R²-G2 | R³-G2 |
| E-3 | R¹-G3 | Ar¹-G2 | R⁴-G3 | Ar²-G2 | L-G3 | R²-G2 | R³-G3 |
| E-4 | R¹-G3 | Ar¹-G3 | R⁴-G4 | Ar²-G2 | L-G3 | R²-G2 | R³-G3 |
| E-5 | R¹-G4 | Ar¹-G3 | R⁴-G4 | Ar²-G2 | L-G3 | R²-G2 | R³-G3 |
| E-6 | R¹-G4a | Ar¹-G3 | R⁴-G4 | Ar²-G2 | L-G3 | R²-G2 | R³-G4 |
| E-7 | R¹-G5 | Ar¹-G3 | R⁴-G4 | Ar²-G2 | L-G3 | R²-G2 | R³-G4 |
| E-8 | R¹-G3 | Ar¹-G3 | R⁴-G4 | Ar²-G2a | L-G3 | R²-G2 | R³-G3 |
| E-9 | R¹-G4 | Ar¹-G3 | R⁴-G4 | Ar²-G2a | L-G3 | R²-G2 | R³-G3 |
| E-10 | R¹-G4a | Ar¹-G3 | R⁴-G4 | Ar²-G2a | L-G3 | R²-G2 | R³-G4 |
| E-11 | R¹-G5 | Ar¹-G3 | R⁴-G4 | Ar²-G2a | L-G3 | R²-G2 | R³-G4 |
| E-12 | R¹-G4a | Ar¹-G3 | R⁴-G4 | Ar²-G3a | L-G4a | R²-G3 | R³-G4 |
| E-13 | R¹-G5 | Ar¹-G3 | R⁴-G5 | Ar²-G3a | L-G4a | R²-G3 | R³-G4 |
| E-14 | R¹-G4a | Ar¹-G3 | R⁴-G4 | Ar²-G3a | L-G4a | R²-G3 | R³-G5 |
| E-15 | R¹-G5 | Ar¹-G3 | R⁴-G5 | Ar²-G3a | L-G4a | R²-G3 | R³-G5 |
| E-16 | R¹-G4a | Ar¹-G3 | R⁴-G5 | Ar²-G3a | L-G5 | R²-G3 | R³-G4 |
| E-17 | R¹-G5 | Ar¹-G3 | R⁴-G5 | Ar²-G3a | L-G5 | R²-G3 | R³-G5 |
| E-18 | R¹-G5a | Ar¹-G3 | R⁴-G5 | Ar²-G3a | L-G5 | R²-G3 | R³-G5 |

The following preferred embodiments of compounds of the formula (I) are described using generic formulae (I.1) to (I.5), wherein any tautomers and stereoisomers, solvates, hydrates and salts thereof, in particular the pharmaceutically acceptable salts thereof, are encompassed.

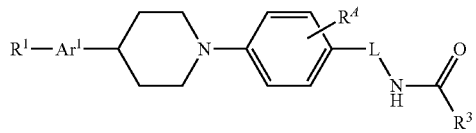
(I.1)

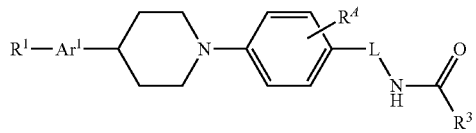
(I.1a)

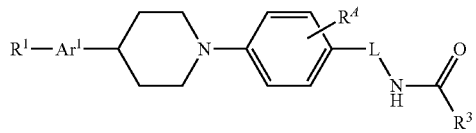
(I.1b)

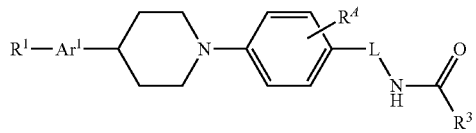
(I.1c)

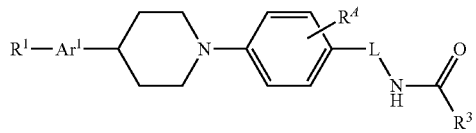
(I.1d)

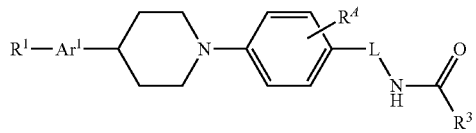
(I.2)

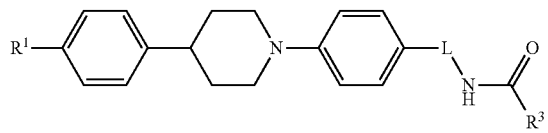
(I.2a)

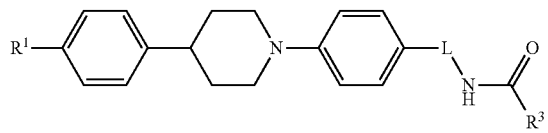
(I.2b)

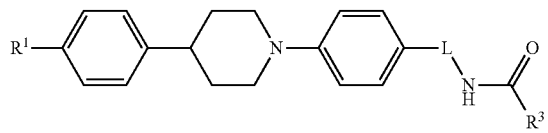
(I.2c)

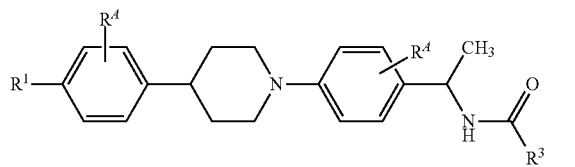
(I.3)

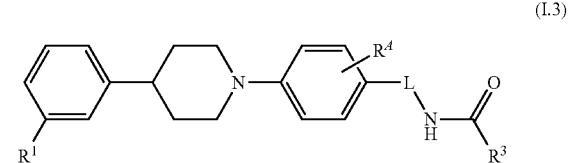
(I.3a)

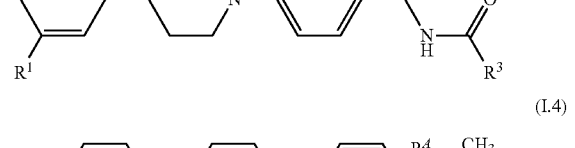
(I.4)

-continued (I.5)

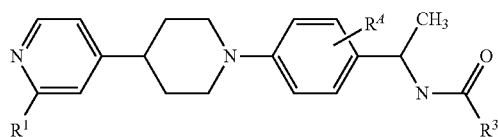

wherein in each of the above formulae (I.1) to (I.5), the groups $Ar^1$, $R^4$, $R^1$, $R^3$ and L are defined as hereinbefore and hereinafter.

Preferred embodiments of the above formulae (I.1) to (I.5) according to the present invention are set forth in the following table, wherein each group $Ar^1$, $R^4$, $R^1$, $R^3$ and L of each embodiment is defined according to the definitions set forth hereinbefore and wherein all other substituents of the formula (I) are defined according to the definitions set forth hereinbefore. Preferred embodiments include:

| Embodiment | Formula | $Ar^1$ | $R^4$ | $R^1$ | $R^3$ | L |
|---|---|---|---|---|---|---|
| E-A | (I.1) | $Ar^1$-G3 | $R^4$-G4 | $R^1$-G4 | $R^3$-G3 | L-G3a |
| E-B | (I.1) | $Ar^1$-G3 | $R^4$-G4 | $R^1$-G4 | $R^3$-G5 | L-G3a |
| E-C | (I.1) | $Ar^1$-G3 | $R^4$-G4 | $R^1$-G4 | $R^3$-G4 | L-G4 |
| E-D | (I.1) | $Ar^1$-G3 | $R^4$-G4 | $R^1$-G5 | $R^3$-G3 | L-G3a |
| E-E | (I.1) | $Ar^1$-G3 | $R^4$-G4 | $R^1$-G5 | $R^3$-G4 | L-G4 |
| E-F | (I.1) | $Ar^1$-G4 | $R^4$-G4 | $R^1$-G4 | $R^3$-G3 | L-G3a |
| E-G | (I.1) | $Ar^1$-G4 | $R^4$-G4 | $R^1$-G4 | $R^3$-G3 | L-G4 |
| E-H | (I.1) | $Ar^1$-G4 | $R^4$-G4 | $R^1$-G4 | $R^3$-G4 | L-G4 |
| E-I | (I.1) | $Ar^1$-G4a | — | $R^1$-G4 | $R^3$-G4 | L-G4 |
| E-J | (I.1) | $Ar^1$-G4a | — | $R^1$-G5 | $R^3$-G5 | L-G4 |
| E-K | (I.1) | $Ar^1$-G5a | — | $R^1$-G5 | $R^3$-G5 | L-G4 |
| E-L | (I.1a) | $Ar^1$-G3 | $R^4$-G4 | $R^1$-G4 | $R^3$-G3 | L-G3a |
| E-M | (I.1a) | $Ar^1$-G5a | — | $R^1$-G4 | $R^3$-G4 | L-G4 |
| E-N | (I.1b) | $Ar^1$-G4b | $R^4$-G4 | $R^1$-G4 | $R^3$-G3 | — |
| E-O | (I.1b) | $Ar^1$-G4b | $R^4$-G4 | $R^1$-G5 | $R^3$-G4 | — |
| E-P | (I.1b) | $Ar^1$-G4b | $R^4$-G4 | $R^1$-G5 | $R^3$-G5 | — |
| E-Q | (I.2) | — | $R^4$-G4 | $R^1$-G4b | $R^3$-G4 | L-G4 |
| E-R | (I.2) | — | $R^4$-G4 | $R^1$-G4b | $R^3$-G6 | L-G4 |
| E-S | (I.2a) | — | — | $R^1$-G4 | $R^3$-G4 | L-G4a |
| E-T | (I.2a) | — | — | $R^1$-G4 | $R^3$-G6 | L-G4a |
| E-U | (I.2b) | — | $R^4$-G4 | $R^1$-G4 | $R^3$-G4 | — |
| E-V | (I.2b) | — | $R^4$-G4 | $R^1$-G4 | $R^3$-G6 | — |
| E-W | (I.2c) | — | — | $R^1$-G4 | $R^3$-G4 | — |
| E-X | (I.2c) | — | — | $R^1$-G4 | $R^3$-G6 | — |
| E-Y | (I.3) | — | $R^4$-G5 | $R^1$-G5 | $R^3$-G6b | L-G5a |
| E-Z | (I.3a) | — | $R^4$-G5 | $R^1$-G5 | $R^3$-G6b | — |
| E-AA | (I.4) | — | $R^4$-G5 | $R^1$-G5a | $R^3$-G6a | — |
| E-BB | (I.5) | — | $R^4$-G5 | $R^1$-G5a | $R^3$-G6a | — | including any tautomers and stereoisomers, solvates, hydrates and salts thereof, in particular the pharmaceutically acceptable salts thereof.

A preferred embodiment of the present invention concerns those compounds of general formula (I), wherein
$Ar^1$ is selected from the group $Ar^1$-G4b consisting of:

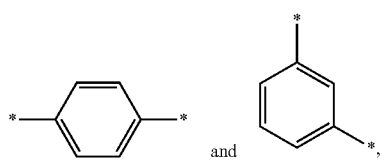

wherein the beforementioned 1,4-phenylene group is optionally substituted with F, —$CH_3$ or —$OCH_3$;

$Ar^2$ is selected from the group $Ar^2$-G3 consisting of:

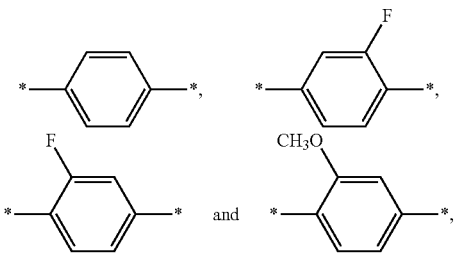

wherein the asterisk to the left side of each group indicates the bond which is connected to the piperidine ring of the core structure of the formula (I), and the asterisk to the right side of each group indicates the bond which is connected to L;

L is selected from the group L-G5a consisting of:

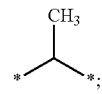

$R^1$ is selected from the group $R^1$-G5a consisting of: $C_{1-4}$-alkyl-O—, $C_{3-4}$-cycloalkyl-O— and $C_{3-4}$-cycloalkyl-$CH_2$—O—,
 wherein each alkyl or cycloalkyl may be optionally substituted with one to three F atoms;
$R^2$ is selected from the group $R^2$-G3 consisting of: H; and
$R^3$ is selected from the group $R^3$-G5 consisting of:
$C_{1-3}$-alkyl, —O—$CH_3$, cyclopropyl, $R^{N1}R^{N2}$N—, morpholinyl, heteroaryl and heteroaryl-$CH_2$—,
 wherein each alkyl may be optionally substituted with one to three F atoms or one CN, OH, —O—$CH_3$ and —S—$CH_3$, and
 wherein each cycloalkyl may be optionally substituted with one CN, or —$CH_3$, and
 wherein each heteroaryl group is selected from the group consisting of pyrrolyl, pyrazolyl, oxazoly, thiazolyl and pyridinyl, and
 wherein each heteroaryl group may be optionally substituted with one or two substituents independently selected from the group consisting of —$CH_3$ and —NH—C(=O)—$CH_3$, and
 wherein $R^{N1}$ is selected from the group consisting of H and $C_{1-2}$-alkyl, and,
 wherein $R^{N2}$ is selected from the group consisting of H, $C_{1-3}$-alkyl and pyridinyl;
and the tautomers, enantiomers and pharmaceutically acceptable salts thereof.

A more preferred embodiment of the present invention concerns those compounds of general formula (I), wherein
$Ar^1$ is selected from the group $Ar^1$-G4b consisting of:

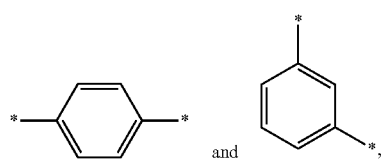

wherein the beforementioned 1,4-phenylene group is optionally substituted with F, —CH$_3$ or —OCH$_3$;
Ar$^2$ is selected from the group Ar$^2$-G3 consisting of:

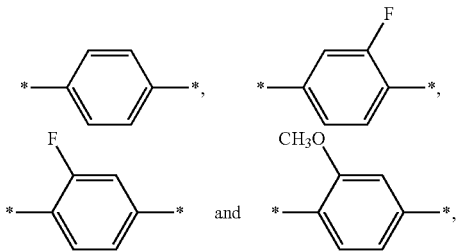

wherein the asterisk to the left side of each group indicates the bond which is connected to the piperidine ring of the core structure of the formula (I), and the asterisk to the right side of each group indicates the bond which is connected to L;
L is selected from the group L-G5a consisting of:

R$^1$ is selected from the group R$^1$-G5a consisting of:
C$_{1-4}$-alkyl-O—, C$_{3-4}$-cycloalkyl-O— and C$_{3-4}$-cycloalkyl-CH$_2$—O—,
wherein each cycloalkyl may be optionally substituted with one or two F atoms;
R$^2$ is selected from the group R$^2$-G3 consisting of: H; and
R$^3$ is selected from the group R$^3$-G6 consisting of:
—CH$_3$, cyclopropyl and —N(CH$_3$)$_2$;
and the tautomers, enantiomers and pharmaceutically acceptable salts thereof.

An even more preferred embodiment of the present invention concerns those compounds of general formula (I), wherein
Ar$^1$ is selected from the group Ar$^1$-G6 consisting of:

Ar$^2$ is selected from the group Ar$^2$-G3a consisting of:

L is selected from the group L-G5a consisting of:

R$^1$ is selected from the group R$^1$-G5a consisting of:
C$_{1-4}$-alkyl-O—, C$_{3-4}$-cycloalkyl-O— and C$_{3-4}$-cycloalkyl-CH$_2$—O—,
wherein each cycloalkyl may be optionally substituted with one or two F atoms;
R$^2$ is selected from the group R$^2$-G3 consisting of: H; and
R$^3$ is selected from the group R$^3$-G6 consisting of:
—CH$_3$, cyclopropyl and —N(CH$_3$)$_2$;
and the tautomers, enantiomers and pharmaceutically acceptable salts thereof.

Particularly preferred compounds, including their tautomers and stereoisomers, the salts thereof, or any solvates or hydrates thereof, are described in the experimental section hereinafter.

Synthesis Schemes

The compounds according to the invention may be obtained using methods of synthesis which are known to the one skilled in the art and described in the literature of organic synthesis. Preferably the compounds are obtained analogously to the methods of preparation explained more fully hereinafter, in particular as described in the experimental section.

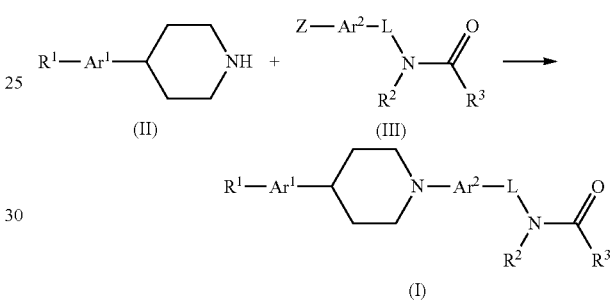

Compounds of general formula (I) may be prepared by palladium-mediated Buchwald reactions or copper-mediated Ullmann reactions of aryl halogenides or aryl triflates (III) with piperidines (II) wherein Z is a leaving group which for example denotes Cl, Br, I or OTf (triflate).

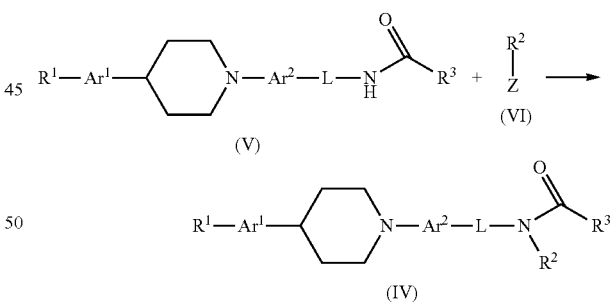

Compounds of general formula (IV) may be prepared by reaction of amides (V) with alkylating reagents R$^2$Z (VI) after deprotonation with bases such as sodium hydride wherein Z is a leaving group which for example denotes Cl, Br, I, mesylate or triflate.

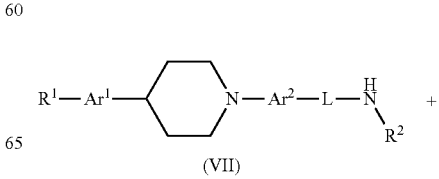

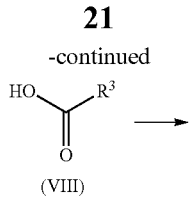

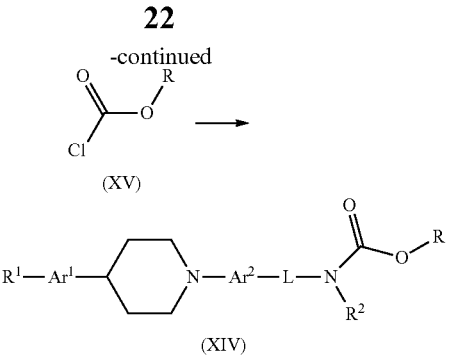

Compounds of general formula (IV) may be prepared by amide coupling reactions of amines (VII) with carboxylic acids (VIII) mediated by coupling reagents such as eg TBTU, HOBt, HATU, CDT or CDI.

Compounds of general formula (XIV), wherein R is $C_{1-4}$-alkyl, may be prepared by urethane forming reactions such as reaction of amines (X) with chloro formates (XV).

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

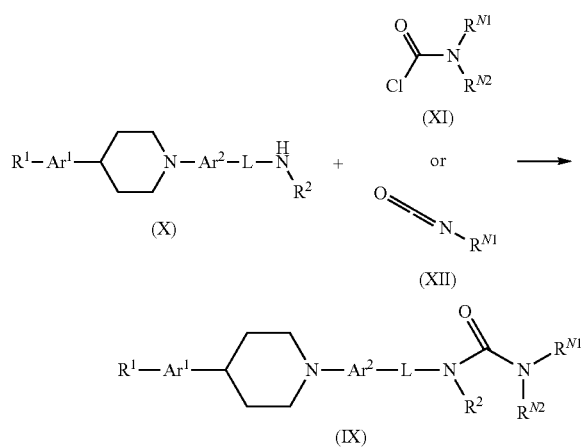

Compounds of general formula (IX) may be prepared by urea forming reactions such as reaction of amines (X) with carbamoyl chlorides (XI) or isocyanates (VII).

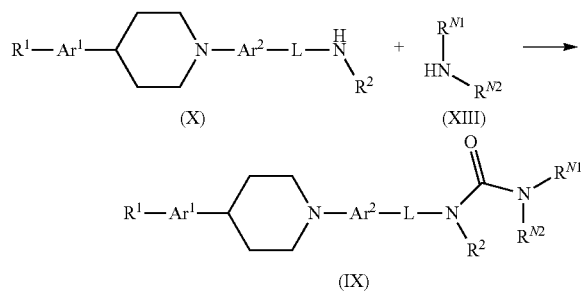

Alternatively, compounds of general formula (IX) may be prepared by reaction of amines (X) with amines (XIII) after reaction with reagents such as CDI or CDT.

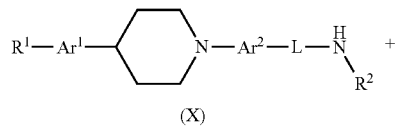

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of acetyl-CoA carboxylase(s) (ACC) with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

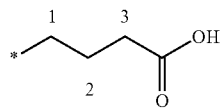 [SMILES: *CCCC(=O)O]

wherein the carboxy group is attached to the third carbon atom of the propyl group. The terms "1-methylpropyl-", "2,2-dimethylpropyl-" or "cyclopropylmethyl-" group represent the following groups:

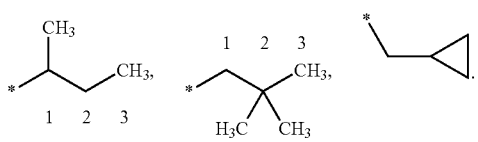

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent.

Salts of other acids than those mentioned above which for example are useful for purifying or isolating the compounds of the present invention also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —($CH_2$)—, —($CH_2$—$CH_2$)—, —($CH(CH_3)$)—, —($CH_2$—$CH_2$—$CH_2$)—, —($C(CH_3)_2$)—, —($CH(CH_2CH_3)$)—, —($CH(CH_3)$—$CH_2$)—, —($CH_2$—$CH(CH_3)$)—, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —($CH_2$—$CH(CH_2CH_3)$)—, —($CH(CH_2CH_3)$—$CH_2$)—, —($CH(CH_2CH_2CH_3)$)—, —($CHCH(CH_3)_2$)— and —$C(CH_3)(CH_2CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —$CH$=$CH_2$, —$CH$=$CH$—$CH_3$, —$CH_2$—$CH$=$CH_2$.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes —CH=CH—, —CH=CH—CH$_2$—, —CH$_2$—CH=CH—.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —C≡CH, —C≡C—CH$_3$, —CH$_2$—C≡CH.

The term "$C_{2-n}$-alkynylene" is used for a group as defined in the definition for "$C_{1-n}$-alkylene" with at least two carbon atoms, if at least two of those carbon atoms of said group are bonded to each other by a triple bond. For example the term $C_{2-3}$-alkynylene includes —C≡C—, —=C—CH$_2$—, —CH$_2$—C≡C—.

The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cylcoalkyl, $C_{3-10}$-cycloalkenyl, octahydropentalenyl, octahydroindenyl, decahydronaphthyl, indanyl, tetrahydronaphthyl. Most preferably the term $C_{3-n}$-carbocyclyl denotes $C_{3-n}$-cylcoalkyl, in particular $C_{3-7}$-cycloalkyl.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "$C_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or S(O)$_r$ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or S(O)$_r$ with r=0, 1 or 2 which in addition may have a carbonyl group. The term "heterocyclyl" is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

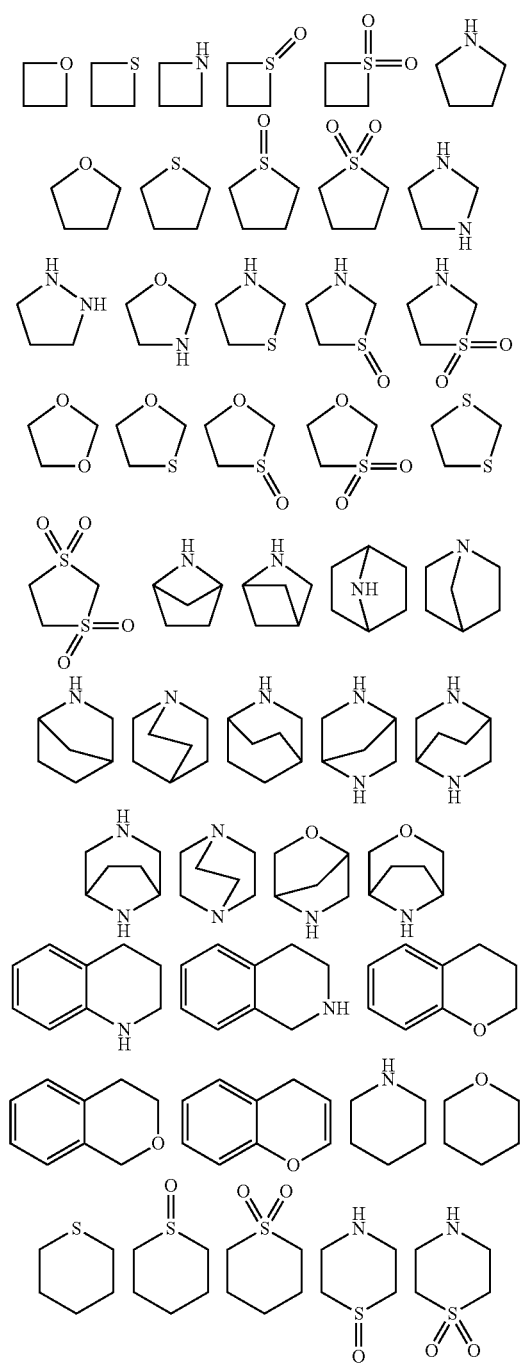

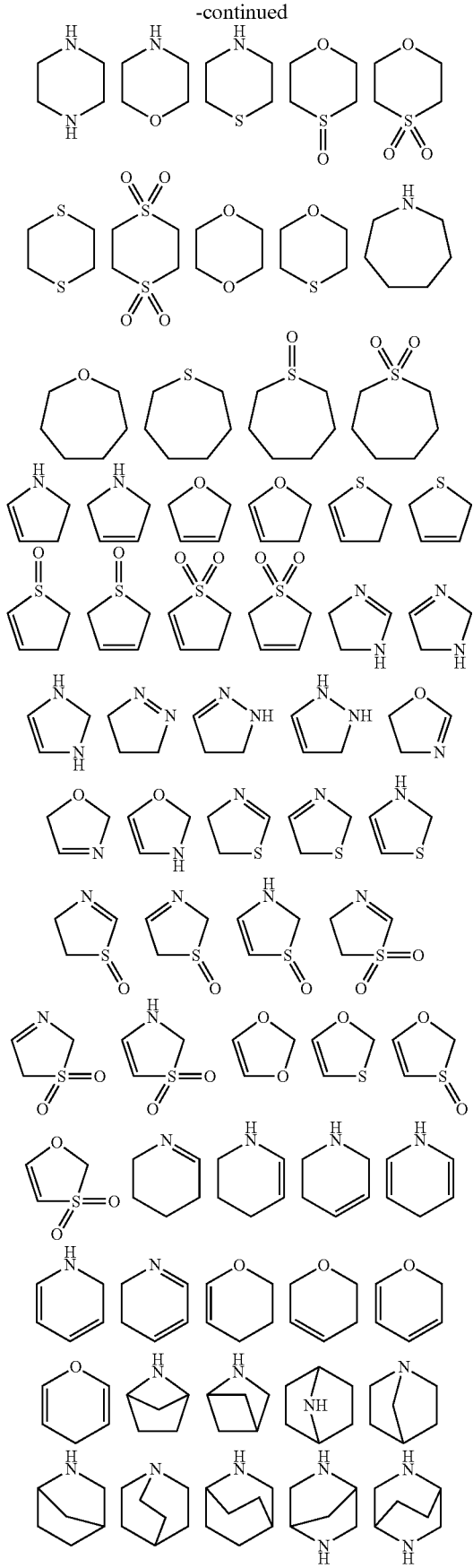
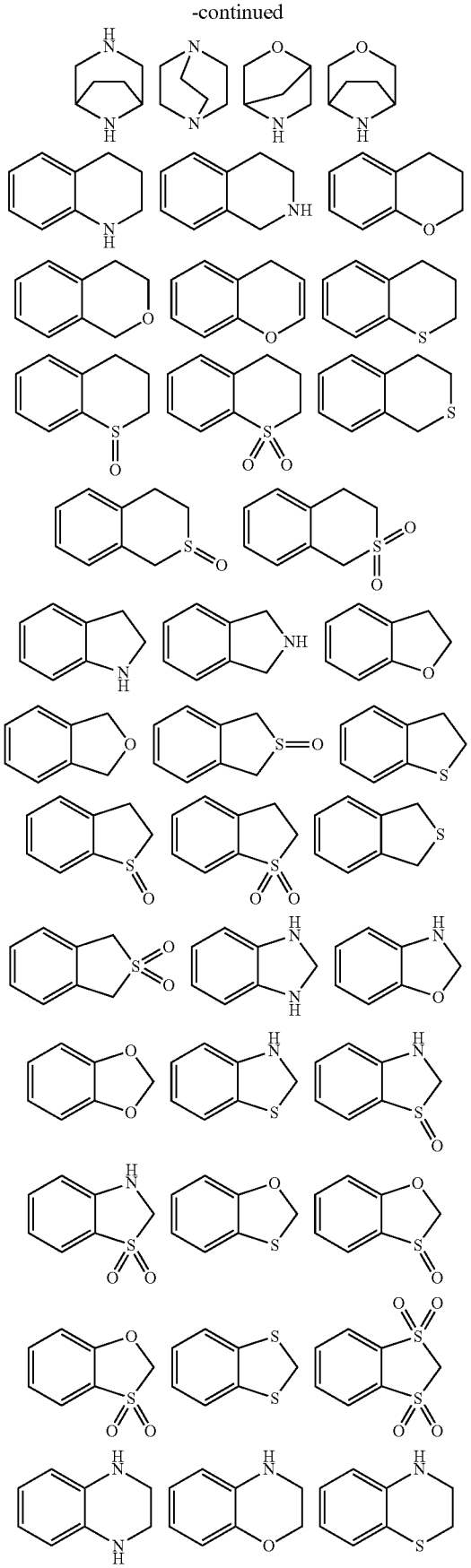

-continued

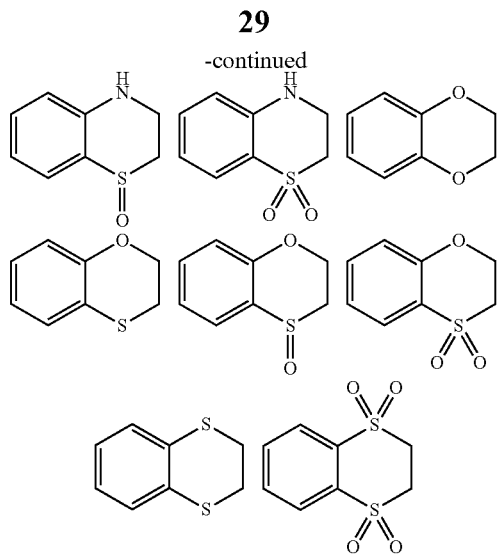

The term "heteroaryl" means a mono- or polycyclic, preferably mono- or bicyclic-ring system containing one or more heteroatoms selected from N, O or $S(O)_r$ with r=0, 1 or 2 wherein at least one of the heteroatoms is part of an aromatic ring, and wherein said ring system may have a carbonyl group. More preferably the term "heteroaryl" as used herein, either alone or in combination with another radical, means a mono- or bicyclic-ring system containing 1, 2, 3 or 4 heteroatoms selected from N, O or $S(O)_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

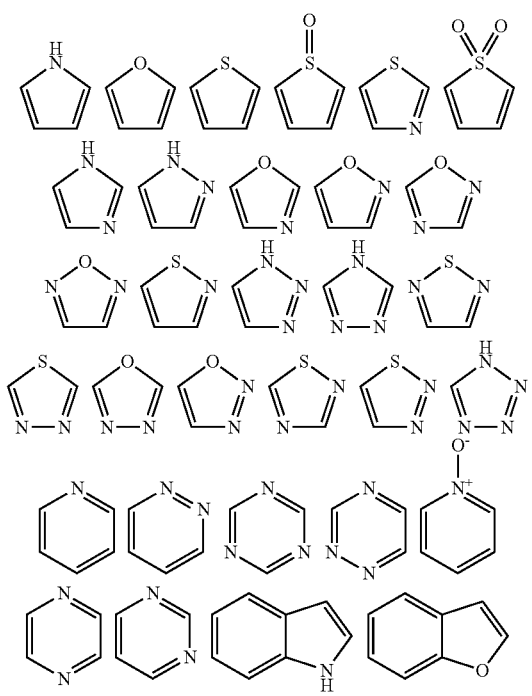

-continued

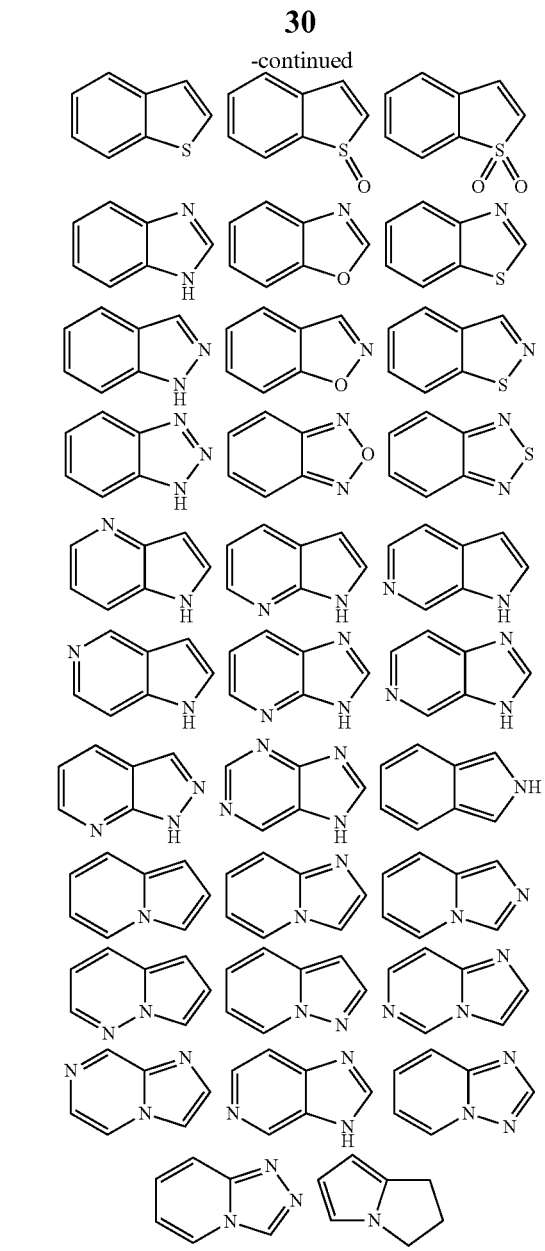

All rests and substituents as defined hereinbefore and hereinafter may be substituted with one or more F atoms. Preferred fluorinated alkyl groups are fluoromethyl, difluoromethyl and trifluoromethyl. Preferred fluorinated alkoxy resp. alkyl-O— groups are fluoromethoxy, difluoromethoxy and trifluoromethoxy.

Many of the terms given above may be used repeatedly in the definition of a formula or group and in each case have one of the meanings given above, independently of one another.

Pharmacological Activity

The activity of the compounds of the invention may be demonstrated using the following ACC2 assay:

Spectrophotometric 384 Well Assay

Malonyl CoA formation by acetyl CoA carboxylases is stoichiometrically linked to the consumption of ATP. ACC2 activity is measured in a NADH-linked kinetic method measuring ADP generated during the ACC reaction using a coupled lactate dehydrogenase/pyruvate kinase reaction.

For biological testing, a human ACC2 construct which lacks the 128 amino acids at the N-terminus for increased solubility (nt 385-6966 in Genbank entry AJ575592) is cloned. The protein is then expressed in insect cells using a baculoviral expression system. Protein purification is performed by anion exchange.

All compounds are dissolved in dimethyl sulfoxide (DMSO) to a concentration of 10 mM.

Assay reactions are then carried out in 384-well plates, with hACC2 in an appropriate dilution and at final assay concentrations (f.c.) of 100 mM Tris (pH 7.5), 10 mM trisodium citrate, 25 mM KHCO$_3$, 10 mM MgCl$_2$, 0.5 mg/ml BSA, 3.75 mM reduced L-glutathione, 15 U/ml lactate dehydrogenase, 0.5 mM phosphoenolpyruvate, 15 U/ml pyruvate kinase, compounds at different concentrations at final DMSO concentrations of 1%.

The enzymatic reaction is then started by addition of a mixture of NADH, acetyl Coenzyme A (both 200 µM f.c.) and ATP (500 uM f.c.). The decrease of the optical density (slope S) is then determined at 25° C. at a wavelength of 340 nm over 15 minutes in a spectrophotometric reader.

Each assay microtiter plate contains wells with vehicle instead of compound as controls for the non-inhibited enzyme (100% CTL; 'HIGH') and wells without acetyl-CoA as controls for non-specific NADH degradation (0% CTL; 'LOW').

The slope S is used for calculation of % CTL=(S(compound)−S('LOW'))/(S('HIGH')−S('LOW'))*100. Compounds will give values between 100% CTL (no inhibition) and 0% CTL (complete inhibition).

For IC$_{50}$ value determination, the sample slope in the presence of the test compound after subtraction of the low controls (S(compound)−S('LOW')) are used.

An IC$_{50}$ value is derived from the compound slopes at different dosages after subtraction of the low controls (S(compound)−S('LOW')) by non-linear regression curve fitting (equation y=(A+((B−A)/(1+((C/x)^D))))).

The compounds of general formula (I) according to the invention for example have IC$_{50}$ values below 10000 nM, particularly below 1000 nM, preferably below 300 nM.

In the following table the activity expressed as IC$_{50}$ (µM) of compounds according to the invention is presented wherein the IC$_{50}$ values are determined in the ACC2 assay as described hereinbefore. The term "Ex." refers to the example numbers according to the following experimental section.

| Example | IC$_{50}$ [µM] |
|---|---|
| 1.1 | 0.07 |
| 1.2 | 0.15 |
| 1.3 | 0.05 |
| 1.4 | 0.23 |
| 1.5 | 0.88 |
| 1.6 | 1.12 |
| 1.7 | 0.09 |
| 1.8 | 0.68 |
| 1.9 | 0.61 |
| 1.10 | 0.80 |
| 1.11 | 0.44 |
| 1.12 | 3.17 |
| 1.13 | 0.13 |
| 1.14 | 0.45 |
| 1.15 | 1.85 |
| 1.16 | 1.24 |
| 1.17 | 0.82 |
| 1.18 | 0.17 |
| 1.19 | 0.82 |
| 1.20 | 0.66 |
| 1.21 | 0.64 |
| 1.22 | 0.25 |
| 1.23 | 0.26 |
| 1.24 | 0.54 |
| 1.25 | 0.37 |
| 1.26 | 0.34 |
| 1.27 | 2.16 |
| 1.30 | 0.06 |
| 1.31 | 0.15 |
| 1.32 | 0.23 |
| 1.33 | 0.46 |
| 1.40 | 0.24 |
| 1.41 | 1.27 |
| 1.42 | 1.26 |
| 1.43 | 0.16 |
| 1.44 | 0.16 |
| 1.45 | 0.35 |
| 1.46 | 0.37 |
| 1.47 | 0.43 |
| 1.48 | 0.46 |
| 1.50 | 1.15 |
| 1.51 | 4.41 |
| 1.52 | 4.23 |
| 1.60 | 1.22 |
| 1.61 | 4.47 |
| 1.70 | 8.47 |
| 2.1 | 4.15 |
| 2.2 | 0.69 |
| 2.3 | 1.21 |
| 2.4 | 0.71 |
| 2.5 | 6.91 |
| 2.6 | 0.11 |
| 2.7 | 0.52 |
| 3.1 | 2.77 |
| 3.2 | 0.38 |
| 3.3 | 0.76 |
| 3.4 | 4.88 |
| 3.5 | 4.53 |
| 3.6 | 0.20 |
| 3.7 | 1.48 |
| 3.8 | 0.44 |
| 3.9 | 4.98 |
| 4.1 | 1.98 |
| 4.2 | 1.16 |
| 4.3 | 2.36 |
| 4.4 | 3.69 |
| 5.1 | 2.09 |
| 6.1 | 3.43 |

In view of their ability to inhibit acetyl-CoA carboxylase(s), the compounds of general formula (I) according to the invention and the corresponding salts thereof are theoretically suitable for the treatment, including preventative treatment of all those diseases or conditions which may be affected or which are mediated by the inhibition of acetyl-CoA carboxylase(s), in particular ACC2, activity.

Accordingly, the present invention relates to a compound of general formula (I) as a medicament.

Furthermore, the present invention relates to the use of a compound of general formula (I) for the treatment and/or prevention of diseases or conditions which are mediated by the inhibition of acetyl-CoA carboxylase(s), in particular ACC2, in a patient, preferably in a human.

In yet another aspect the present invention relates a method for treating, including preventing a disease or condition mediated by the inhibition of acetyl-CoA carboxylase(s) in a mammal that includes the step of administering to a patient, preferably a human, in need of such treatment a therapeutically effective amount of a compound of the present invention, or a pharmaceutical composition thereof. Diseases and conditions mediated by inhibitors of acetyl-CoA carboxylases embrace metabolic and/or cardiovascular and/or neurodegenerative diseases or conditions.

According to one aspect the compounds of the present invention are particularly suitable for treating diabetes mellitus, in particular Type 2 diabetes, Type 1 diabetes, and diabetes-related diseases, such as is hyperglycemia, metabolic syndrome, impaired glucose tolerance, diabetic neuropathy, diabetic nephropathy, diabetic retinopathy, dyslipidemia, hypertension, hyperinsulinemia, and insulin resistance syndrome, hepatic insulin resistance, including complications such as macro- and microvascular disorders, including thromboses, hypercoagulable and prothrombotic states (arterial and venous), high blood pressure, coronary artery disease and heart failure, increased abdominal girth, hypercoagulability, hyperuricemia, micro-albuminemia.

According to another aspect the compounds of the present invention are particularly suitable for treating overweight, obesity, including visceral (abdominal) obesity, nonalcoholic fatty liver disease (NAFLD) and obesity related disorders, such as for example weight gain or weight maintenance Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$ or greater.

According to another aspect the compounds of the present invention are particularly suitable for treating, including preventing, or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, pancreatic beta cell degeneration and diabetic complications (such as macro- and microvascular disorders, atherosclerosis, coronary heart disease, stroke, peripheral vascular disease, nephropathy, hypertension, neuropathy, and retinopathy).

In addition the compounds of the present invention are suitable for treating dyslipidemias in general and more specifically elevated lipid concentrations in the blood and in tissues, dysregulation of LDL, HDL and VLDL, in particular high plasma triglyceride concentrations, high postprandial plasma triglyceride concentrations, low HDL cholesterol concentration, low apoA lipoprotein concentrations, high LDL cholesterol concentrations, high apoB lipoprotein concentrations, including atherosclerosis, coronary heart disease, cerebrovascular disorders, diabetes mellitus, metabolic syndrome, obesity, insulin resistance and/or cardiovascular disorders.

ACC inhibition may lead to a centrally stimulating effect on food intake. Therefore compounds of the present invention may be suitable for treating eating disorders such as anorexia nervosa.

In addition the compounds of the present invention may provide neuroprotective effects in patients with Parkinson's disease, Alzheimer's disease, hypoxia, ischemia, amyotrophic lateral sclerosis or glioma and may improve cognitive scores in Alzheimer's diseases patients.

Further diseases and conditions mediated by inhibitors of acetyl-CoA carboxylases embrace but are not limited to:

A. disorders of fatty acid metabolism and glucose utilization disorders; disorders in which insulin resistance is involved;
B. hepatic disorders and conditions related thereto, including: fatty liver, hepatic steatosis, non-alcoholic hepatitis, non-alcoholic steatohepatitis (NASH), alcoholic hepatitis, acute fatty liver, fatty liver of pregnancy, drug-induced hepatitis, iron storage diseases, hepatic fibrosis, hepatic cirrhosis, hepatoma, viral hepatitis;
C. skin disorders and conditions and those associated with polyunsaturated fatty acids, such as
 eczema, acne, sebaceous gland diseases, psoriasis, keloid scar formation or prevention, other diseases related to mucous membrane fatty acid composition;
D. primary hypertriglyceridemia or secondary hypertriglyceridemias following familial histiocytic reticulosis, lipoprotein lipase deficiency, hyperlipo-proteinemias, apolipoprotein deficiency (e.g. apoCII or apoE deficiency);
E. diseases or conditions related to neoplastic cellular proliferation, for example benign or malignant tumors, cancer, neoplasias, metastases, carcinogenesis;
F. diseases or conditions related to neurological, psychiatric or immune disorders or conditions;
G. other diseases or conditions in which inflammatory reactions, cell differentiation and/or other ACC-mediated aspects may for example be involved are:
 atherosclerosis such as, for example (but not restricted thereto), coronary sclerosis including angina pectoris or myocardial infarction, stroke, ischemic, stroke and transient ischemic attack (TIA),
 peripheral occlusive disease,
 vascular restenosis or reocclusion,
 chronic inflammatory bowel diseases such as, for example, Crohn's disease and ulcerative colitis,
 pancreatitis,
 sinusitis,
 retinopathy, ischemic retinopathy,
 adipose cell tumors,
 lipomatous carcinomas such as, for example, liposarcomas,
 solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas, breast cancer (in particular breast cancer with BRCA1 mutations), etc.,
 tumors in which ACC is up regulated,
 acute and chronic myeloproliferative disorders and lymphomas, angiogenesis
 neurodegenerative disorders including Alzheimer's disease, multiple sclerosis, Parkinson's disease, epilepsy,
 erythemato-squamous dermatoses such as, for example, psoriasis,
 acne vulgaris,
 other skin disorders and dermatological conditions which are modulated by PPAR,
 eczemas and neurodermatitis,
 dermatitis such as, for example, seborrheic dermatitis or photodermatitis,
 keratitis and keratoses such as, for example, seborrheic keratoses, senile keratoses, actinic keratoses, photo-induced keratoses or keratosis follicularis,
 keloids and keloid prophylaxis,
 bacterial infections,
 fungal infections,
 warts, including condylomata or condylomata acuminata
 viral infections such as, for example, human hepatitis B virus (HBV), hepatitis C virus (HCV), West Nile virus (WNV) or Dengue virus, human Immunodeficiency virus (HIV), poxvirus and Vaccinia virus (VV), HCMV, influenza A, human papilloma viral (HPV). venereal papillomata, viral warts such as, for example, molluscum contagiosum, leukoplakia, papular dermatoses such as, for example, lichen planus,
skin cancer such as, for example, basal-cell carcinomas, melanomas or cutaneous T-cell lymphomas,
localized benign epidermal tumors such as, for example, keratoderma, epidermal naevi,
chilblains;
high blood pressure,
polycystic ovary syndrome (PCOS),
asthma,
cystic fibrosis,
osteoarthritis,
lupus erythematosus (LE) or inflammatory rheumatic disorders such as, for example rheumatoid arthritis,
vasculitis,
wasting (cachexia),
gout,
ischemia/reperfusion syndrome,
acute respiratory distress syndrome (ARDS)
viral diseases and infections
lipodystrophy and lipodystrophic conditions, also for treating adverse drug effect;
myophathies and lipid myopathis (such as carnitine palmitoyltransferase I or II deficiency);
H. formation of muscles and a lean body or muscle mass formation.

The dose range of the compounds of general formula (I) applicable per day is usually from 0.001 to 10 mg per kg body weight of the patient, preferably from 0.01 to 8 mg per kg body weight of the patient. Each dosage unit may conveniently contain 0.1 to 1000 mg of the active substance, preferably it contains between 0.5 to 500 mg of the active substance.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent. According to one embodiment the additional therapeutic agent is selected from the group of therapeutic agents useful in the treatment of diseases or conditions associated with metabolic diseases or conditions such as for example diabetes mellitus, obesity, diabetic complications, hypertension, hyperlipidemia.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, agents for the treatment of malignant tumors, antithrombotic agents, agents for the treatment of heart failure and agents for the treatment of complications caused by diabetes or associated with diabetes.

Suitable anti-obesity agents include 11beta-hydroxy steroid dehydrogenase-1 (11beta-HSD type 1) inhibitors, stearoyl-CoA desaturase-1 (SCD-1) inhibitors, MCR-4 agonists, cholecystokinin-A (CCK-A) agonists, monoamine reuptake inhibitors, sympathomimetic agents, beta3 adrenergic agonists, dopamine agonists, melanocyte-stimulating hormone analogs, 5HT2c agonists, melanin concentrating hormone antagonists, leptin (the OB protein), leptin analogs, leptin agonists, galanin antagonists, lipase inhibitors, anorectic agents, neuropeptide-Y antagonists (e.g., NPYY5 antagonists), $PY_{y3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors, human agouti-related protein (AGRP) inhibitors, ghrelin antagonists, GOAT (Ghrelin O-Acyltransferase) inhibitors, histamine 3 antagonists or inverse agonists, neuromedin U agonists, MTP/ApoB inhibitors (e.g., gut-selective MTP inhibitors), opioid antagonists, orexin antagonists, and the like.

Preferred anti-obesity agents for use in the combination aspects of the present invention include gut-selective MTP inhibitors CCKa agonists, 5HT2c agonists, MCR4 agonists, lipase inhibitors, opioid antagonists, oleoyl-estrone, obinepitide, pramlintide (Symlin®), tesofensine (NS2330), leptin, liraglutide, bromocriptine, orlistat, exenatide (Byetta®), AOD-9604 (CAS No. 221231-10-3) and sibutramine.

Suitable anti-diabetic agents include sodium-glucose co-transporter (SGLT) inhibitors, 11beta-hydroxy steroid dehydrogenase-1 (11beta-HSD type 1) inhibitors, phosphodiesterase (PDE) 10 inhibitors, diacylglycerol acyltransferase (DGAT) 1 or 2 inhibitors, sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, an alpha-amylase inhibitors (e.g., tendamistat, trestatin and AL-3688), alpha-glucoside hydrolase inhibitors (e.g., acarbose), alpha-glucosidase inhibitors (e.g., adiposine, camiglibose, emiglitate, miglitol, voglibose, pradimicin-Q, and salbostatin), PPAR gamma agonists (e.g., balaglitazone, ciglitazone, darglitazone, englitazone, isaglitazone, pioglitazone, rosiglitazone and troglitazone), PPAR alpha/gamma agonists (e.g., CLX-0940, GW-1536, GW-20 1929, GW-2433, KRP-297, L-796449, LR-90, MK-0767 and SB-219994), biguanides (e.g., metformin), GLP-1 derivatives, glucagon-like peptide 1 (GLP-1) agonists (e.g., Byetta™, exendin-3 and exendin-4), GLP-1 receptor and glucagon receptor co-agonists, glucagon receptor antagonists, GIP receptor antagonists, protein tyrosine phosphatase-1 B (PTP-1 B) inhibitors (e.g., trodusquemine, hyrtiosal extract), SIRT-1 activators (e.g. reservatrol), dipeptidyl peptidease IV (DPP-IV) inhibitors (e.g., sitagliptin, vildagliptin, alogliptin, linagliptin and saxagliptin), insulin secretagogues, GPR119 agonists, GPR40 agonists, TGR5 agonists, MNK2 inhibitors, GOAT (Ghrelin O-Acyltransferase) inhibitors, fatty acid oxidation inhibitors, A2 antagonists, c-jun amino-terminal kinase (JNK) inhibitors, insulins, insulin derivatives, fast acting insulins, inhalable insulins, oral insulins, insulin mimetics, glycogen phosphorylase inhibitors, VPAC2 receptor agonists and glucokinase activators.

Preferred anti-diabetic agents are metformin, glucagon-like peptide 1 (GLP-1) agonists (e.g., Byetta™), GLP-1 receptor and glucagon receptor co-agonists, sodium-glucose co-transporter (SGLT) inhibitors, 11beta-hydroxy steroid dehydrogenase-1 (11beta-HSD type 1) inhibitors and DPP-IV inhibitors (e.g. sitagliptin, vildagliptin, alogliptin, linagliptin and saxagliptin).

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of the acetyl-CoA carboxylase(s), in particular ACC2, in particular diseases or conditions as described hereinbefore and hereinafter.

In yet another aspect the present invention relates a method for treating, including preventing a disease or condition mediated by the inhibition of acetyl-CoA carboxylase(s) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Further aspects of the invention include the use of a compound according to the invention or a salt thereof as a crop protection agent to combat and/or prevent fungal infestations, or to control other pests such as weeds, insects, or acarids that are harmful to crops. Another aspect of the invention relates to the use of a compound according to the invention or a salt thereof for controlling and/or preventing plant pathogenic microorganisms, for example plant pathogenic fungi. Therefore one aspect of the invention is a compound according to the formula (I) or a salt thereof for use as a fungicide, insecticide, acaricide and/or herbicide. Another aspect of the invention relates to an agricultural composition comprising a compound of the present invention together with one or more suitable carriers. Another aspect of the invention relates to an agricultural composition comprising a compound of the present invention in combination with at least one additional fungicide and/or systemically acquired resistance inducer together with one or more suitable carriers.

EXAMPLES

The Examples that follow are intended to illustrate the present invention without restricting it. The terms "ambient temperature" and "room temperature" are used interchangeably and designate a temperature of about 20° C.

Preliminary Remarks:

As a rule, 1H-NMR and/or mass spectra have been obtained for the compounds prepared. The $R_f$ values are determined using Merck silica gel 60 $F_{254}$ plates and UV light at 254 nm.

Experimental Part

The following abbreviations are used above and hereinafter:

| | |
|---|---|
| aq. | aqueous |
| ACN | acetonitrile |
| BINAP | 2,2'-bis(diphenylphosphino)-1,1'-binaphthalene |
| CDI | N,N-carbonyldiimidazole |
| CDT | N,N-carbonylditriazole |
| DBU | 1,8-diazabicycloundec-7-ene |
| DCM | dichloromethane |
| DIPEA | N,N-diisopropylethylamine |
| DMF | N,N-dimethylformamide |
| dppf | 1,1'-bis[diphenylphosphino]-ferrocene |
| EtOAc | ethyl acetate |
| FA | formic acid |
| HATU | 2-(1H-7-azabenzotriazol-1-yl)-1,1,3,3-tetramethyluronium hexafluorophosphate |
| HOBt | N-Hydroxybenzotriazole |
| MeOH | methanol |
| n.d. | not determined |
| PE | petroleum ether |
| rt | room temperature (about 20° C.) |
| sat. | saturated |
| TEA | triethylamine |
| TFA | trifluoroacetic acid |
| THF | tetrahydrofuran |
| TBTU | 2-(1H-benzotriazol-1-yl)-1,1,3,3-tetramethyluronium tetrafluoroborat |

Analytic Methods

1) HPLC

Method A

Analytical Column: XBridge C18, 3 × 30 mm, 2.5 μm (Waters)

| time [min] | Vol % [H$_2$O, 0.1% TFA] | Vol % [methanol] | Flow [mL/min] | Temperature [° C.] |
|---|---|---|---|---|
| 0.0 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.70 | 0 | 100 | 2.9 | 60 |

Method B

| time (min) | Vol % water (incl. 0.2% NH$_4$OH) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters) 2.5 μm; 3.0×30 mm; column temperature: 60° C.; flow: 1.3 mL/min.

Method C

| time (min) | Vol % water (incl. 0.2% NH₄OH) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters) 2.5 μm; 3.0×30 mm; column temperature: 40° C.; flow: 1.3 mL/min.

Method D

| time (min) | Vol % 0.01M NH₄OAc | Vol % ACN |
|---|---|---|
| 0.0 | 90 | 10 |
| 8.0 | 10 | 90 |
| 15.0 | 10 | 90 |
| 15.1 | 90 | 10 |

Analytical column: XBridge C8 (Waters) 5.0 μm; 4.6×150 mm; column temperature: rt; flow: 1.0 mL/min.

Method E

| time (min) | Vol % 0.01M NH₄OAc | Vol % ACN |
|---|---|---|
| 0.0 | 70 | 30 |
| 8.0 | 10 | 90 |
| 15.0 | 10 | 90 |
| 15.1 | 70 | 30 |

Analytical column: XBridge C8 (Waters) 5.0 μm; 4.6×150 mm; column temperature: rt; flow: 1.0 mL/min.

Method F

| time (min) | Vol % water (incl. 0.05% TFA) | Vol % ACN |
|---|---|---|
| 0.0 | 70 | 30 |
| 8.0 | 10 | 90 |
| 15.0 | 10 | 90 |
| 15.1 | 70 | 30 |

Analytical column: Kromasil C18 5.0 μm; 4.6×250 mm; column temperature: rt; flow: 1.0 mL/min.

Method G

| time (min) | Vol % water (incl. 0.1% FA) | Vol % acetonitrile (incl. 0.1% FA) |
|---|---|---|
| 0.0 | 95 | 5 |
| 0.1 | 95 | 5 |
| 3.1 | 2 | 98 |
| 4.5 | 2 | 98 |
| 5.0 | 95 | 5 |

Analytical column: X-terra MS C18 (Waters) 2.5 μm; 4.6×30 mm; column temperature: rt; flow: 1.0 mL/min.

Method H

Analytical Column: Venusil XBP-C18, 2.1 × 50 mm, 5 μm (Agela)

| time [min] | Vol % [H₂O, 0.0375% TFA] | Vol % [ACN, 0.018% TFA] | Flow [mL/min] | Temperature [° C.] |
|---|---|---|---|---|
| 0.0 | 90 | 10 | 1 | 50 |
| 2.00 | 20 | 80 | 1 | 50 |
| 2.48 | 20 | 80 | 1 | 50 |
| 2.50 | 90 | 10 | 1 | 50 |
| 3.00 | 90 | 10 | 1 | 50 |

Method I

Analytical Column: Venusil MP-C18, 4.6 × 50 mm, 5 μm (Agela)

| time [min] | Vol % [H₂O, 0.0675% TFA] | Vol % [ACN, 0.625% TFA] | Flow [mL/min] | Temperature [° C.] |
|---|---|---|---|---|
| 0.0 | 100 | 0 | 1 | 40 |
| 4.00 | 40 | 60 | 1 | 40 |
| 5.20 | 40 | 60 | 1 | 40 |
| 5.21 | 100 | 0 | 1 | 40 |
| 7.00 | 100 | 0 | 1 | 40 |

Method J

Analytical Column XBridge C18, 2.1 × 50 mm, 3.5 μm (Waters)

| time [min] | Vol % [ACN, 0.1% FA] | Vol % [H₂O, 0.1% FA] | Flow [mL/min] | Temperature [° C.] |
|---|---|---|---|---|
| 0.0 | 5 | 95 | 0.8 | 35 |
| 3.50 | 98 | 2 | 0.8 | 35 |
| 6.00 | 98 | 2 | 0.8 | 35 |

Method K

Analytical Column XBridge C18, 3 × 30 mm, 2.5 μm (Waters)

| time [min] | Vol % [H₂O, 0.2% NH₄OH] | Vol % [methanol] | Flow [mL/min] | Temperature [° C.] |
|---|---|---|---|---|
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

Method L

| time (min) | Vol % water (incl. 0.05% TFA) | Vol % ACN |
|---|---|---|
| 0.0 | 70 | 30 |
| 8.0 | 10 | 90 |
| 15.0 | 10 | 90 |
| 15.1 | 70 | 30 |

Analytical column: XBridge C18 (Waters) 3.5 μm; 4.6×150 mm; column temperature: rt; flow: 1.0 mL/min.

Method M

| time [min] | Vol % [H₂O, 0.1% NH₄OH] | Vol % [methanol] | Flow [mL/min] | Temperature [° C.] |
|---|---|---|---|---|
| 0.0 | 80 | 20 | 2.0 | 60 |
| 1.7 | 0 | 100 | 2.0 | 60 |
| 2.5 | 0 | 100 | 2.0 | 60 |
| 2.6 | 80 | 20 | 2.0 | 60 |

Analytical Column: XBridge C18, 4.6 × 50 mm, 3.5 μm (Waters)

Method N

| time [min] | Vol % [H₂O, 0.1% NH₄OH] | Vol % [methanol] | Flow [mL/min] | Temperature [° C.] |
|---|---|---|---|---|
| 0.0 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.70 | 0 | 100 | 2.9 | 60 |

Analytical Column: XBridge C18, 3 × 30 mm, 2.5 μm (Waters)

Method O

| time [min] | Vol % [H₂O, 0.1% TFA] | Vol % [ACN] | Flow [mL/min] | Temperature [° C.] |
|---|---|---|---|---|
| 0.0 | 95 | 5 | 1.5 | 60 |
| 0.7 | 1 | 99 | 1.5 | 60 |
| 0.8 | 1 | 99 | 1.5 | 60 |
| 0.81 | 95 | 5 | 1.5 | 60 |

Analytical Column: Ascentis Express C18, 2.1 × 50 mm, 2.7 μm

Method P

| time [min] | Vol % [H₂O, 0.1% TFA] | Vol % [methanol] | Flow [mL/min] | Temperature [° C.] |
|---|---|---|---|---|
| 0.0 | 80 | 20 | 2.0 | 60 |
| 1.7 | 0 | 100 | 2.0 | 60 |
| 2.5 | 0 | 100 | 2.0 | 60 |
| 2.6 | 80 | 20 | 2.0 | 60 |

Analytical Column: Sunfire C18, 4.6 × 50 mm, 3.5 μm (Waters)

Method Q

| time [min] | Vol % [H₂O, 0.1% TFA] | Vol % [methanol] | Flow [mL/min] | Temperature [° C.] |
|---|---|---|---|---|
| 0.00 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

Analytical Column: Sunfire C18, 3.0 × 30 mm, 2.5 μm (Waters)

Method R

| time [min] | Vol % [H₂O, 0.1% TFA] | Vol % [methanol] | Flow [mL/min] | Temperature [° C.] |
|---|---|---|---|---|
| 0.00 | 95 | 5 | 4.0 | 60 |
| 0.05 | 95 | 5 | 3.0 | 60 |
| 2.05 | 0 | 100 | 3.0 | 60 |
| 2.10 | 0 | 100 | 4.5 | 60 |
| 2.40 | 0 | 100 | 4.5 | 60 |

Analytical Column: XBridge C18, 4.6 × 30 mm, 2.5 μm (Waters)

Method S

| time [min] | Vol % [H₂O, 0.1% TFA] | Vol % [methanol] | Flow [mL/min] | Temperature [° C.] |
|---|---|---|---|---|
| 0.00 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

Analytical Column: Stable Bond C18, 3.0 × 30 mm, 1.8 μm (Waters)

Preparation of Starting Compounds

Example I

Example I.1

1-Bromo-4-cyclobutoxybenzene

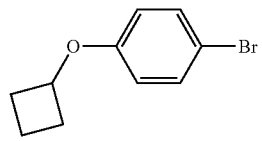 [SMILES: Brc1ccc(OC2CCC2)cc1]

2.50 g (14.5 mmol) 4-bromophenol, 2.05 mL (21.7 mmol) cyclobutylbromide and 7.99 g (57.8 mmol) $K_2CO_3$ are dissolved in 25 mL DMF and stirred at 120° C. for 12 h. Afterwards the reaction mixture is diluted with water and extracted with EtOAc. The organic layer is dried over $MgSO_4$ and the solvent is removed in vacuo. The crude product is used without further purification.

$C_{10}H_{11}BrO$ (M=227.1 g/mol)

ESI-MS: 227 $[M+H]^+$ $R_t$ (HPLC): 1.39 min (method A)

The following compounds are prepared analogously to example I.1:

| Ex. | Starting material | Reagent | Product structure | ESI-MS [m/z] | $R_t$(HPLC) [min] (method) |
|---|---|---|---|---|---|
| I.1 | HO–C₆H₄–Br | cyclobutyl-bromide | cyclobutyl-O–C₆H₄–Br | 227 [M + H]⁺ | 1.39 (A) |
| I.2 | 3-methoxy-4-bromophenol | ethyl-bromide | 1-ethoxy-3-methoxy-4-bromobenzene | 231 [M + H]⁺ | 2.00 (C) |
| I.3 | 3-fluoro-4-bromophenol | cyclopropylmethyl chloride | cyclopropylmethoxy-3-fluoro-4-bromobenzene | 244/246 [M]⁺ | 2.08 (B) |
| I.4 | 3-bromophenol | cyclobutyl-chloride | 1-cyclobutoxy-3-bromobenzene | n.d. | 8.79 (E) |
| I.5* | 2-methyl-4-bromophenol | n-propyl-bromide | 1-propoxy-2-methyl-4-bromobenzene | n.d. | 2.31 (C) |

*$R_f$(TLC): 0.79 (silica gel, cyclohexane/EtOAc 9:1)

Example II

Example II.1

4-(4-Ethoxy-phenyl)-piperidine

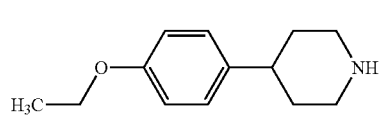

a) 4-(4-Ethoxy-phenyl)-pyridine

Under inert gas atmosphere 88 mg (0.12 mmol) PdCl₂(dppf)ₓCH₂Cl₂, 13.6 mL (27.2 mmol) 2N sodium carbonate solution and 1.64 g (13.3 mmol) pyridine-4-boronic acid are added to 3.00 g (12.1 mmol) 1-ethoxy-4-iodo-benzene in 18 mL 1,4-dioxane and 6 mL methanol. The mixture is stirred for 2 d at reflux. After that time, water is added. The precipitate is filtered off, taken up in DCM and extracted with water. The organic layer is dried over sodium sulphate and the solvent is evaporated. The residue is purified by column chromatography (silica gel; gradient DCM:MeOH 100:0→95:5) to yield the desired product which is directly used in the next reaction step.

b) 4-(4-Ethoxy-phenyl)-piperidine 410 mg (2.06 mmol) 4-(4-Ethoxy-phenyl)-pyridine in 10 mL acetic acid are hydrogenated (3 bar) for 9 h at rt using 50 mg platinum(IV) oxide. After that time, the catalyst is filtered off and the solvent is evaporated. The residue is taken up in 1N NaOH and extracted with EtOAc. The organic layer is dried over sodium sulphate and the solvent is evaporated. The residue is purified by column chromatography (silica gel; DCM:MeOH 9:1, then THF:MeOH:NH₄OH 1:1:0.1) to yield the desired product.

$C_{13}H_{19}NO$ (M=205.3 g/mol)
ESI-MS: 206 [M+H]⁺
$R_t$ (HPLC): 1.86 min (method C)

The following compounds are prepared analogously to example 11.1:

| Example | Starting material | Product structure | EI-MS [m/z] | R$_t$(HPLC) [min] (method) |
|---|---|---|---|---|
| II.1 | (4-iodo-phenyl ethoxymethyl ether) | (4-(4-ethoxymethoxyphenyl)piperidine) | 206 [M + H]$^+$ | 1.86 (C) |
| II.2 | (4-bromo-3-fluoro-phenyl cyclopropylmethyl ether) | (fluoro-cyclopropylmethoxy-phenyl piperidine) | 250 [M + H]$^+$ | 6.37 (D) |
| II.3 | (4-bromo-phenyl propyl ether) | (4-propoxyphenyl piperidine) | 220 [M + H]$^+$ | 6.12 (D) |
| II.4 | (4-bromo-phenyl cyclopropylmethyl ether) | (4-cyclopropylmethoxy-phenyl piperidine) | 232 [M + H]$^+$ | 3.82 (L) |
| II.5 | (3-bromo-phenyl cyclopropylmethyl ether) | (3-cyclopropylmethoxy-phenyl piperidine) | 232 [M + H]$^+$ | 3.84 (L) |
| II.6 | (4-bromo-phenyl isopropyl ether) | (4-isopropoxyphenyl piperidine) | 220 [M + H]$^+$ | 3.90 (E) |
| II.7 | (3-bromo-phenyl cyclobutyl ether) | (3-cyclobutoxyphenyl piperidine) | 206 [M + H]$^+$ | 1.31 (A) |
| II.8 | (4-bromo-phenyl cyclobutyl ether) | (4-cyclobutoxyphenyl piperidine) | 232 [M + H]$^+$ | 4.32 (E) |
| II.9 | (4-bromo-3-methyl-phenyl ethyl ether) | (methyl-ethoxy-phenyl piperidine) | 234 [M + H]$^+$ | 6.51 (D) |

-continued

| Example | Starting material | Product structure | EI-MS [m/z] | $R_t$(HPLC) [min] (method) |
|---|---|---|---|---|
| II.10 | 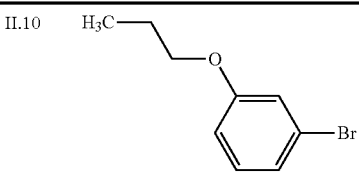 | 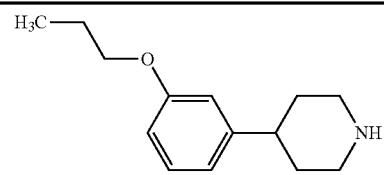 | 220 [M + H]⁺ | 5.27 (F) |
| II.11 | 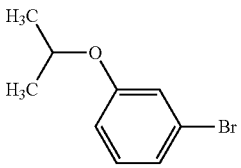 | 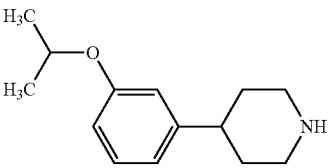 [SMILES: CC(C)Oc1cccc(C2CCNCC2)c1] | 220 [M + H]⁺ | 1.25 (A) |
| II.12 | 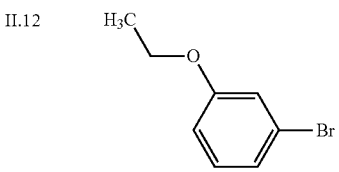 | 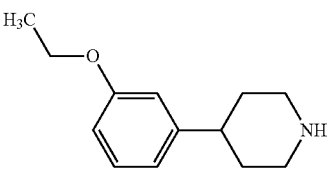 | 206 [M + H]⁺ | 1.18 (A) |
| II.13 | 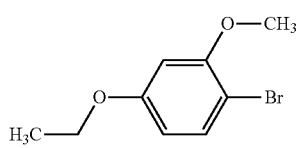 | 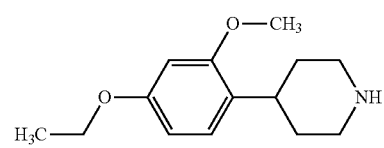 | 236 [M + H]⁺ | 2.32 (H) |

Example III

Example III.1

(S)—N-[1-(4-Bromo-phenyl)-ethyl]-acetamide

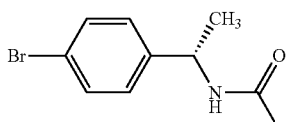

23.6 mL (250 mmol) acetic anhydride are added to 50.0 g (250 mmol) (S)-1-(4-bromophenyl)-ethylamine in 200 mL DCM while keeping the reaction temperature below 30° C. Stirring is continued for 12 h at rt. After that time, saturated NaHCO₃-solution is added. The organic layer is separated, washed with water, dried over magnesium sulphate and the solvent is removed by evaporation.

$C_{10}H_{12}BrNO$ (M=242.1 g/mol), ESI-MS: 242 [M+H]⁺
$R_t$ (HPLC): 1.03 min (method N)

The following compounds are prepared analogously to Example III.1:

Example III.2

N-[2-(4-Bromo-phenyl)-1-methyl-ethyl]-acetamide

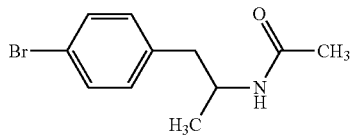

Educt: 2-(4-Bromo-phenyl)-1-methyl-ethylamine (J. Org. Chem. 1985, 50, 133).
$C_{11}H_{14}BrNO$ (M=256.1 g/mol), ESI-MS: 256 [M+H]⁺
$R_t$ (HPLC): 2.60 min (method G)

Example III.3

(S)-Cyclopropanecarboxylic acid [1-(4-bromo-phenyl)-ethyl]amide

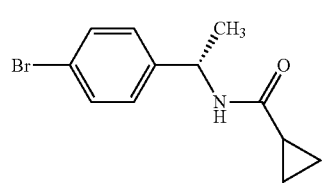

$C_{12}H_{14}BrNO$ (M=268.2 g/mol), ESI-MS: 268 [M+H]⁺
$R_t$ (HPLC): 2.76 min (method G)

Example III.4

N-[3-(4-Bromo-phenyl)-1-methyl-propyl]-acetamide

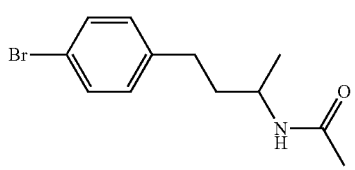

Educt: 3-(4-Bromo-phenyl)-1-methyl-propylamine
$C_{12}H_{16}BrNO$ (M=270.2 g/mol), ESI-MS: 270 [M+H]⁺
$R_t$ (HPLC): 2.11 min (method C)

Example IV

Example IV.1

4-[4-(2,2-Difluoro-cyclopropylmethoxy)-phenyl]-piperidine hydrochloride

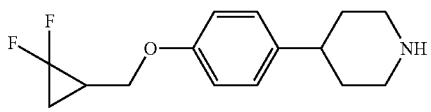

4.48 g (19.2 mmol, 80%) Methanesulfonic acid 2,2-difluoro-cyclopropylmethyl ester are added to 5.93 g (19.2 mmol, 90%) 4-(4-hydroxy-phenyl)-piperidine-1-carboxylic acid tert-butyl ester and 5.36 g (38.5 mmol) $K_2CO_3$ in 60 mL DMF. Stirring is continued for 12 h at 50° C. under inert gas atmosphere. After that time, brine (50 mL) is added and the mixture is extracted with EtOAc (3×50 mL). The organic layer is separated, washed with brine, dried over sodium sulphate and the solvent is removed by evaporation. The residue is purified by column chromatography (silica gel; gradient PE:EtOAc 20:1→10:1). The residue is taken up in 20 mL DCM and 100 mL 4N HCl in EtOAc are added dropwise at 0° C. The mixture is stirred for 12 h at rt. After that time, the solvent is removed in vacuo to yield the desired product.

$C_{15}H_{19}F_2NO$ (M=267.3 g/mol), EI-MS: 267 [M]$^+$ $R_t$ (HPLC): 3.34 min (method I)

Example V

Example V.1

(S)-[1-(4-Bromo-phenyl)-ethyl]-carbamic acid methyl ester

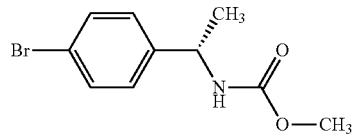

17.2 g (105 mmol) CDT are added to a mixture of 20.0 g (100 mmol) (S)-1-(4-bromophenyl)-ethylamine and 17.6 mL (125 mmol) TEA in 300 mL dichloromethane at 0° C. Stirring is continued for 15 min at 5° C. After that time, the solvent is removed in vacuo and taken up in 50 mL methanol. 33.4 mL (180 mmol) sodium methoxide in methanol (30%) are added and stirring is continued for 48 h at rt. After that time, the solvent is removed in vacuo, the residue is taken up in ethyl acetate and washed with sat. $KHSO_4$-solution (2×) and water. The organic layer is dried over magnesium sulphate and the solvent is removed by evaporation.

$C_{10}H_{12}BrNO_2$ (M=258.1 g/mol), ESI-MS: 258 [M+H]$^+$ $R_t$ (HPLC): 2.60 min (method B)

The following compounds are prepared analogously to Example V.1:

Example V.2

(S)-3-[1-(4-Bromo-phenyl)-ethyl]-1,1-dimethyl-urea

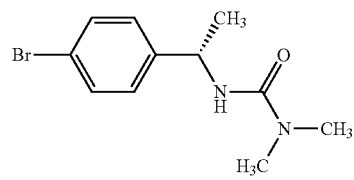

Educt: dimethylamine
$C_{11}H_{15}BrN_2O$ (M=271.2 g/mol), ESI-MS: 271 [M+H]$^+$
$R_t$ (HPLC): 1.68 min (method B)

Example VI

Example VI.1

6-Ethoxy-3',6'-dihydro-2'H-[3,4']bipyridinyl-1'-carboxylic acid tert-butyl ester

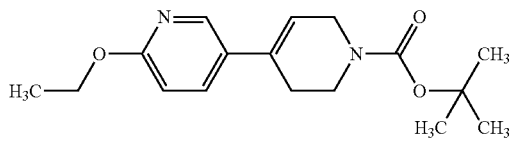

Under inert gas atmosphere 5.00 g (23.3 mmol) 5-bromo-2-ethoxy-pyridine are added to a mixture of 7.19 g (23.3 mmol) 4-(4,4,5,5-tetramethyl-[1,3,2]dioxaborolan-2-yl)-3,6-dihydro-2H-pyridine-1-carboxylic acid tert-butyl ester, 95 mg (1.2 mmol) $PdCl_2(dppf)_x CH_2Cl_2$ and 15.2 g (46.5 mol) $Cs_2CO_3$ in 50 mL DMF and 10 mL $H_2O$. The mixture is stirred for 12 h at 80° C. After that time, the solvent is evaporated, the residue taken up in DCM and washed with brine. After drying over sodium sulphate, the solvent is removed in vacuo and the residue is purified by column chromatography (silica gel; gradient PE/EtOAc 20:1→10:1) to yield the desired product which was directly used in the next step.

$C_{17}H_{24}N_2O_3$ (M=304.4 g/mol)
$R_f$ (TLC): 0.30 (silica gel, PE/ethyl acetate 20:1)

The following compounds are prepared analogously to Example VI.1:

Example VI.2

2'-Ethoxy-3,6-dihydro-2H-[4,4']bipyridinyl-1-carboxylic acid tert-butyl ester

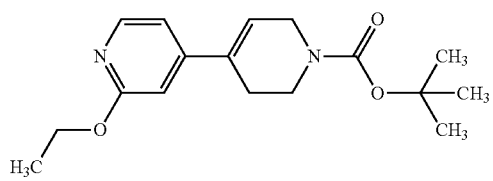 [SMILES: CCOc1cc(C2=CCN(C(=O)OC(C)(C)C)CC2)ccn1]

Educt: 4-bromo-2-ethoxy-pyridine
$C_{17}H_{24}N_2O_3$ (M=304.4 g/mol)
$R_f$ (TLC): 0.30 (silica gel, PE/ethyl acetate 20:1)

Example VII

Example VII.1

6-Ethoxy-3',4',5',6'-tetrahydro-2'H-[3,4']bipyridinyl-1'-carboxylic acid tert-butyl ester

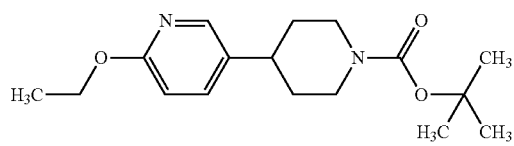

5.80 g (17.9 mmol) 6-Ethoxy-3,6'-dihydro-2'H-[3,4']bipyridinyl-1'-carboxylic acid tert-butyl ester (VI.1) in 60 mL ethanol are hydrogenated (40 psi) for 12 h at rt using 500 mg palladium on charcoal (10%). After that time, the catalyst is filtered off and the solvent is evaporated. The residue is purified by column chromatography (silica gel; gradient PE/EtOAc 20:1→10:1) to yield the desired product which is directly used in the next step.

$C_{17}H_{26}N_2O_3$ (M=306.4 g/mol)

$R_f$(TLC): 0.20 (silica gel, PE/ethyl acetate 20:1)

The following compounds are prepared analogously to Example VII.1:

Example VII.2

2'-Ethoxy-3,4,5,6-tetrahydro-2H-[4,4']bipyridinyl-1-carboxylic acid tert-butyl ester

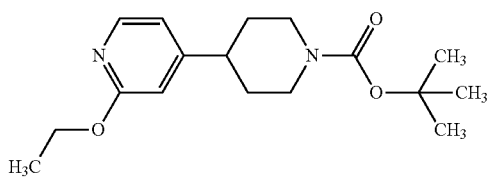

Educt: VI.2
$C_{17}H_{26}N_2O_3$ (M=306.4 g/mol)
$R_f$(TLC): 0.20 (silica gel, PE/ethyl acetate 20:1)

Example VIII

Example VIII.1

6-Ethoxy-1',2',3',4',5',6'-hexahydro-[3,4']bipyridinyl hydrochloride

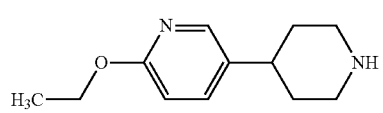

To 4.30 g (13.9 mmol) 6-Ethoxy-3',4',5',6'-tetrahydro-2'H-[3,4]bipyridinyl-1'-carboxylic acid tert-butyl ester (VII.1) in 10 mL EtOAc are added 120 mL 4N HCl in EtOAc. The mixture is stirred for 12 h at rt. After that time, the solvent is evaporated to yield the desired product.

$C_{12}H_{18}N_2O$*HCl (M=242.7 g/mol)

$R_f$(TLC): 0.10 (silica gel, DCM/methanol 10:1)

The following compounds are prepared analogously to Example VIII.1:

Example VIII.2

2'-Ethoxy-1,2,3,4,5,6-hexahydro-[4,4']bipyridinyl

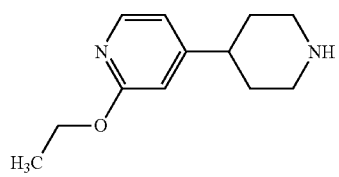

Educt: VII.2
$C_{12}H_{18}N_2O$*HCl (M=242.7 g/mol)
$R_f$(TLC): 0.10 (silica gel, DCM/methanol 10:1)

Example IX

Example IX.1

2-Methyl-propane-2-sulfonic acid 4-bromo-3-fluoro-benzylideneamide

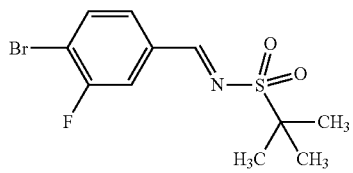

11.1 g (91.0 mmol) 2-Methyl-2-propanesulfinamide are added to 16.5 g (76.0 mmol) 4-bromo-3-fluoro-benzaldehyde and 34.6 g (152 mmol) titanium(IV) ethoxide in 100 mL THF. Stirring is continued for 1.5 h at 50° C. After that time, the mixture is poured into brine. The mixture is filtered over celite and the filtrate is transferred to a separation funnel. The organic layer is separated, dried over magnesium sulphate and the solvent is removed by evaporation. The residue is purified by column chromatography (silica gel; gradient hexane/EtOAc 1:0→3:2) to yield the desired product.

$C_{11}H_{13}BrFNOS$ (M=306.2 g/mol), ESI-MS: 306/308 [M+H]$^+$ $R_f$(TLC): 0.30 (silica gel, hexane/EtOAc 4:1)

The following compounds are prepared analogously to Example IX.1:

Example IX.2

2-Methyl-propane-2-sulfonic acid 4-bromo-2-fluoro-benzylideneamide

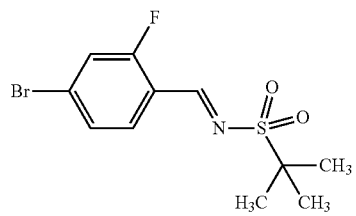 [SMILES: CC(C)(C)S(=O)(=O)/N=C/c1ccc(Br)cc1F]

Educt: 4-bromo-2-fluoro-benzaldehyde
$C_{11}H_{13}BrFNOS$ (M=306.2 g/mol), ESI-MS: 306/308 [M+H]$^+$

Example IX.3

2-Methyl-propane-2-sulfonic acid 4-bromo-3-methoxy-benzylideneamide

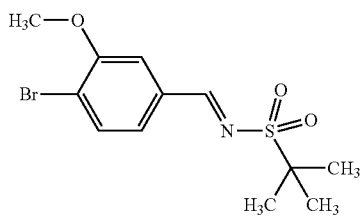 [SMILES: COc1cc(/C=N/S(=O)(=O)C(C)(C)C)ccc1Br]

Educt: 4-bromo-3-methoxy-benzaldehyde
$C_{12}H_{16}BrNO_2S$ (M=318.2 g/mol), ESI-MS: 318/320 [M+H]$^+$
$R_f$(TLC): 0.60 (silica gel, hexane/EtOAc 2:1)

Example X

Example X.1

2-Methyl-propane-2-sulfonic acid [1-(4-bromo-3-fluoro-phenyl)-ethyl]amide

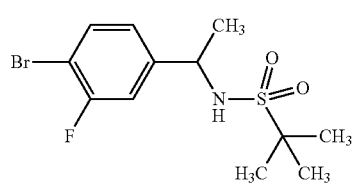

Under inert gas atmosphere 37.2 mL (112 mmol) of a 3N solution of methyl magnesium bromide in THF are added dropwise to 17.1 g (55.8 mmol) 2-methyl-propane-2-sulfonic acid 4-bromo-3-fluoro-benzylideneamide (IX.1) in 170 mL THF at −78° C. The cooling bath is removed and stirring is continued for 2 h. After that time, the mixture is poured into sat. NH$_4$Cl-solution (300 mL) and extracted with EtOAc. The organic layer is separated, washed with brine and dried over sodium sulphate. The solvent is removed by evaporation to yield the desired product.
$C_{12}H_{17}BrFNOS$ (M=322.2 g/mol), ESI-MS: 322/324 [M+H]$^+$ The following compounds are prepared analogously to Example X.1:

Example X.2

2-Methyl-propane-2-sulfonic acid [1-(4-bromo-2-fluoro-phenyl)-ethyl]amide

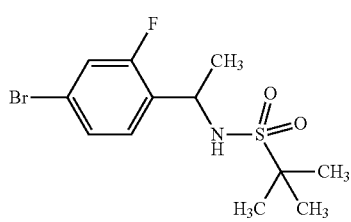 [SMILES: CC(NS(=O)(=O)C(C)(C)C)c1ccc(Br)cc1F]

Educt: IX.2
$C_{12}H_{17}BrFNOS$ (M=322.2 g/mol), ESI-MS: 322/324 [M+H]$^+$

Example X.3

2-Methyl-propane-2-sulfonic acid [1-(4-bromo-3-methoxy-phenyl)-ethyl]amide

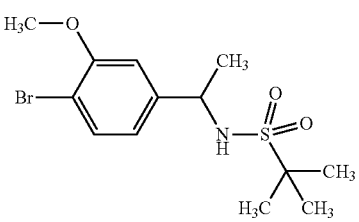 [SMILES: COc1cc(C(C)NS(=O)(=O)C(C)(C)C)ccc1Br]

Educt: IX.3
$C_{13}H_{20}BrNO_2S$ (M=334.3 g/mol), ESI-MS: 334/336 [M+H]$^+$

Example XI

Example XI.1

N-[1-(4-Bromo-3-fluoro-phenyl)-ethyl]acetamide

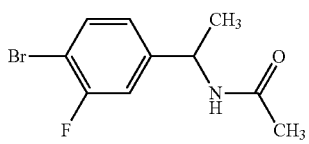

20.0 mL 4N HCl in dioxane are added to 17.2 g (53.4 mmol) 2-methyl-propane-2-sulfonic acid [1-(4-bromo-3-fluoro-phenyl)-ethyl]-amide (X.1) in 150 mL MeOH. Stirring is continued for 1 h. After that time, the mixture is concentrated and the residue is triturated from diethylether (150 mL). The precipitate is filtered off, washed with diethylether and suspended in 250 mL DCM. 8.64 mL (107 mmol) pyridine and 5.29 mL (56.1 mmol) acetic anhydride are added and the mixture is stirred for 12 h at rt. After that time, the mixture is transferred to a separation funnel, washed with 1N HCl (200 mL) and sat. aq. NaHCO3-solution (200 mL) and dried over sodium sulphate. The solvent is removed by evaporation to yield the desired product.

$C_{10}H_{11}BrFNO$ (M=260.1 g/mol), ESI-MS: 260/262 $[M+H]^+$ $R_t$ (HPLC): 2.60 min (method J)

The following compounds are prepared analogously to Example XI.1:

Example XI.2

N-[1-(4-Bromo-2-fluoro-phenyl)-ethyl]acetamide

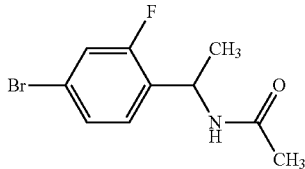

Educt: X.2

$C_{10}H_{11}BrFNO$ (M=260.1 g/mol), ESI-MS: 260/262 $[M+H]^+$ $R_t$ (HPLC): 2.60 min (method J)

Example XI.3

N-[1-(4-Bromo-3-methoxy-phenyl)-ethyl]acetamide

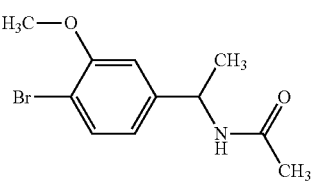

Educt: X.3

$C_{11}H_{14}BrNO_2$ (M=272.1 g/mol), ESI-MS: 272/274 $[M+H]^+$ $R_t$ (HPLC): 2.56 min (method J)

Example XII

Example XII.1

(S)-1-{4-[4-(4-Ethoxy-phenyl)-piperidin-1-yl]-phenyl}-ethylamine hydrochloride

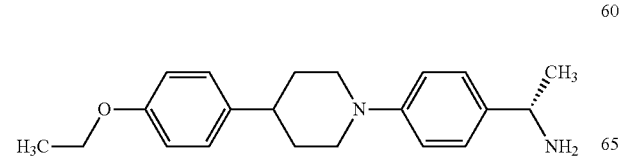

Under inert gas atmosphere 19.47 g (94.86 mmol) 4-(4-ethoxy-phenyl)-piperidine (II.1) are added to a mixture of 29.9 g (99.6 mmol) (S)-1-(4-bromo-phenyl)-ethyl]-carbamic acid tert-butyl ester, 36.5 g (0.38 mol) sodium tert-butyrat, 17.35 g (18.97 mmol) tris-(dibenzylidenaceton)-dipalladium (0) and 14.15 g (47.43 mmol) 2-(di-tert-butylphosphino)biphenyl in 750 mL 1,4-dioxane. The mixture is stirred for 6 h at 50° C. and for additional 5 h at 55° C. After that time, additional 5.00 g (5.47 mmol) tris-(dibenzylidenaceton)-dipalladium(0) and 5.00 g (16.8 mmol) 2-(di-tert-butyl-phosphino)biphenyl in 750 mL 1,4-dioxane are added and stirring is continued for 4 h at 55° C. Finally the mixture is filtered over Celite, the residue washed with ACN (500 mL) and the combined solvent evaporated. The residue is purified by column chromatography (silica gel, 15-50% EtOAc in heptanes). The product is taken up in i-propanol (50 mL) and 100 mL 5-6 N HCl in i-propanol are added. The mixture is stirred for 4 h at rt. After that time, the mixture is concentrated. The residue is triturated with diethylether to yield the desired product.

$C_{21}H_{28}N_2O \cdot HCl$ (M=360.9 g/mol), ESI-MS: 325 $[M+H]^+$ $R_t$ (HPLC): 0.88 min (method Q)

Preparation of Final Compounds

Example 1

Example 1.1

(S)—N-(1-{4-[4-(4-Propoxy-phenyl)-piperidin-1-yl]-phenyl}-ethyl)-acetamide

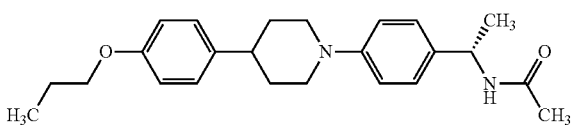

80 mg (0.37 mmol) 4-(4-Propoxy-phenyl)-piperidine (II.3) are added to a mixture of 88 mg (0.37 mmol) (S)—N-[1-(4-bromo-phenyl)-ethyl]-acetamide (III.1), 145 mg (97%, 1.46 mmol) sodium tert-butyrat, 44 mg (0.15 mmol) 2-(di-tert-butylphosphino)biphenyl and 33 mg (0.036 mmol) tris-(dibenzylidenaceton)-dipalladium(0) in 2.0 mL 1,4-dioxane. The mixture is stirred for 12 h at 70° C. After that time, the mixture is filtered over celite, the solvent is removed in vacuo and the residue is purified by HPLC (column: Waters XBridge 5 μM; eluent A: water+0.3% NH4OH, eluent B: MeOH) to yield the desired product.

$C_{24}H_{32}N_2O_2$ (M=380.5 g/mol)

ESI-MS: 381 $[M+H]^+$ $R_t$ (HPLC): 1.29 min (method K)

The following compounds of general formula (I-1) are prepared analogously to Example 1.1, the educts used being shown in the column headed "E 1" and "E 2". Alternatively heating at reaction temperatures of 20-120° C. with or without microwave irradiation is used in the examples below:

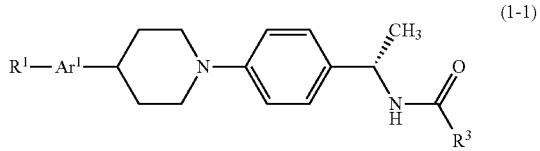

| Ex. | R¹—Ar¹ | R³ | E 1 | E 2 | ESI-MS [m/z] | R$_t$ HPLC [min] (method) |
|---|---|---|---|---|---|---|
| 1.1 | H₃C-O-C₆H₄-* (propoxy phenyl) | *—CH₃ | II.3 | III.1 | 381 [M + H]⁺ | 1.29 (K) |
| 1.2 | H₃C-O-C₆H₄-* (ethoxy phenyl) | *—CH₃ | II.1 | III.1 | 367 [M + H]⁺ | 1.18 (K) |
| 1.3 | H₃C-O-C₆H₃(CH₃)-* (propoxy methylphenyl) | *—CH₃ | II.9 | III.1 | 395 [M + H]⁺ | 1.30 (K) |
| 1.4 | cyclobutyloxy phenyl-* | *—CH₃ | II.8 | III.1 | 393 [M + H]⁺ | 1.30 (K) |
| 1.5 | cyclopropylmethoxy phenyl-* | *—CH₃ | II.5 | III.1 | 393 [M + H]⁺ | 1.26 (K) |
| 1.6 | H₃C-O-C₆H₄-* (3-ethoxy phenyl) | *—CH₃ | II.12 | III.1 | 367 [M + H]⁺ | 1.21 (K) |
| 1.7 | 2,2-difluorocyclopropylmethoxy phenyl-* | *—CH₃ | IV.1 | III.1 | 429 [M + H]⁺ | 1.34 (A) |
| 1.8 | H₃C-O-C₆H₄-* (ethoxy phenyl) | *—cyclopropyl | II.1 | III.3 | 393 [M + H]⁺ | 1.22 (K) |
| 1.9 | isopropoxy phenyl-* | *—N(CH₃)₂ | II.6 | V.2 | 410 [M + H]⁺ | 1.26 (K) |
| 1.10 | isopropoxy phenyl-* | *—cyclopropyl | II.6 | III.3 | 407 [M + H]⁺ | 1.28 (K) |
| 1.11 | H₃C-O-C₆H₃(OCH₃)-* (ethoxy methoxyphenyl) | *—CH₃ | II.13 | III.1 | 397 [M + H]⁺ | 1.35 (A) |

-continued

| Ex. | R¹—Ar¹ | R³ | E 1 | E 2 | ESI-MS [m/z] | R$_t$ HPLC [min] (method) |
|---|---|---|---|---|---|---|
| 1.12 | 2-ethoxypyridin-5-yl | *—CH$_3$ | VIII.1 | III.1 | 368 [M + H]$^+$ | 1.25 (A) |
| 1.13 | 4-(cyclopropylmethoxy)-2-fluorophenyl | *—CH$_3$ | II.2 | III.1 | 412 [M + H]$^+$ | 1.28 (K) |
| 1.14 | 3-cyclobutoxyphenyl | *—CH$_3$ | II.7 | III.1 | 393 [M + H]$^+$ | 1.29 (K) |
| 1.15 | 4-(cyclopropylmethoxy)phenyl | *-cyclopropyl | II.4 | III.3 | 419 [M + H]$^+$ | 1.30 (K) |
| 1.16 | 4-cyclobutoxyphenyl | *-cyclopropyl | II.8 | III.3 | 419 [M + H]$^+$ | 1.33 (K) |
| 1.17 | 4-ethoxyphenyl | *—N(CH$_3$)$_2$ | II.1 | V.2 | 396 [M + H]$^+$ | 1.34 (K) |
| 1.18 | 4-isopropoxyphenyl | *—CH$_3$ | II.6 | III.1 | 381 [M + H]$^+$ | 1.30 (K) |
| 1.19 | 2-ethoxypyridin-4-yl | *—CH$_3$ | VIII.2 | III.1 | 368 [M + H]$^+$ | 1.25 (A) |
| 1.20 | 3-propoxyphenyl | *—CH$_3$ | II.10 | III.1 | 381 [M + H]$^+$ | 1.28 (K) |
| 1.21 | 4-propoxyphenyl | *-cyclopropyl | II.3 | III.3 | 407 [M + H]$^+$ | 1.32 (K) |

-continued

| Ex. | R¹—Ar¹ | R³ | E 1 | E 2 | ESI-MS [m/z] | R_t HPLC [min] (method) |
|---|---|---|---|---|---|---|
| 1.22 | 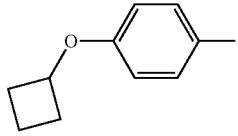 | 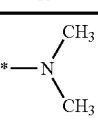 | II.8 | V.2 | 422 [M + H]⁺ | 1.31 (K) |
| 1.23 | 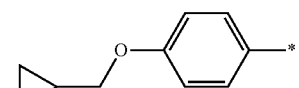 | *—CH₃ | II.4 | III.1 | 393 [M + H]⁺ | 1.26 (K) |
| 1.24 | 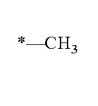 | 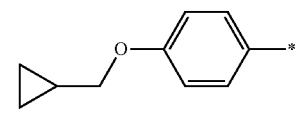 | II.4 | V.2 | 422 [M + H]⁺ | 1.30 (K) |
| 1.25 | 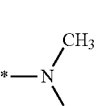 | *—CH₃ | II.11 | III.1 | 381 [M + H]⁺ | 1.36 (K) |
| 1.26 | 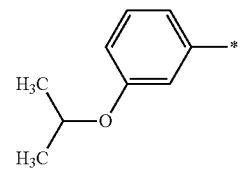 | 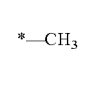 | II.3 | V.2 | 410 [M + H]⁺ | 1.30 (K) |
| 1.27 | 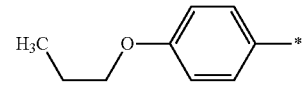 [SMILES: *c1ccc(OCCC)cc1] | *—CH₃ | 4-(4-methoxy-phenyl)-piperidine | III.1 | 353 [M + H]⁺ | 0.89 (S) |

The following compounds of general formula (I-2) are prepared analogously to Example 1.1, the educts used being shown in the column headed "E 1" and "E 2". Alternatively heating at reaction temperatures of 20-120° C. with or without microwave irradiation is used in the examples below:

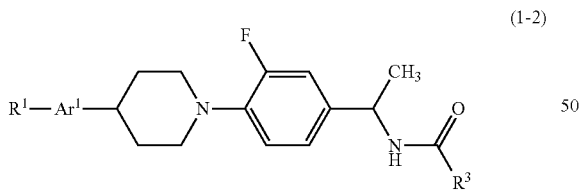

(I-2)

| Ex. | R¹—Ar¹ | R³ | E 1 | E 2 | ESI-MS [m/z] | R_t HPLC [min] (method) |
|---|---|---|---|---|---|---|
| 1.30 | 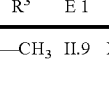 | *—CH₃ | II.9 | XI.1 | 413 [M + H]⁺ | 1.44 (A) |

-continued

| Ex. | R¹—Ar¹ | R³ | E 1 | E 2 | ESI-MS [m/z] | $R_t$ HPLC [min] (method) |
|---|---|---|---|---|---|---|
| 1.31 | (cyclopropylmethoxy-fluorophenyl) | *—CH₃ | II.2 | XI.1 | 429 [M + H]⁺ | 1.43 (A) |
| 1.32 | (ethoxyethoxy-phenyl) H₃C-O-phenyl-* | *—CH₃ | II.3 | XI.1 | 399 [M + H]⁺ | 1.42 (A) |
| 1.33 | (isopropoxy-phenyl) | *—CH₃ | II.6 | XI.1 | 399 [M + H]⁺ | 1.39 (A) |

The following compounds of general formula (I-3) are prepared analogously to Example 1.1, the educts used being shown in the column headed "E 1" and "E 2". Alternatively heating at reaction temperatures of 20-120° C. with or without microwave irradiation is used in the examples below:

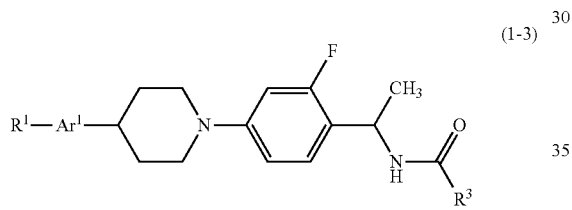

(I-3)

| Ex. | R¹—Ar¹ | R³ | E 1 | E 2 | ESI-MS [m/z] | $R_t$ HPLC [min] (method) |
|---|---|---|---|---|---|---|
| 1.40 | H₃C-O-phenyl-* | *—CH₃ | II.3 | XI.2 | 399 [M + H]⁺ | 1.41 (A) |
| 1.41 | (ethoxy-phenyl) | *—CH₃ | II.12 | XI.2 | 385 [M + H]⁺ | 1.36 (A) |
| 1.42 | (isopropoxy-phenyl) | *—CH₃ | II.11 | XI.2 | 399 [M + H]⁺ | 1.39 (A) |

-continued

| Ex. | R¹—Ar¹ | R³ | E 1 | E 2 | ESI-MS [m/z] | R$_t$ HPLC [min] (method) |
|---|---|---|---|---|---|---|
| 1.43 | 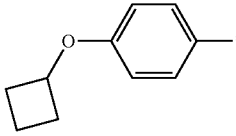 | *—CH₃ | II.8 | XI.2 | 411 [M + H]⁺ | 1.42 (A) |
| 1.44 | 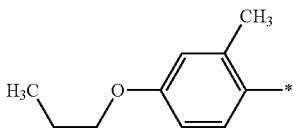 [SMILES: *c1ccc(OCCC)cc1C] | *—CH₃ | II.9 | XI.2 | 413 [M + H]⁺ | 1.44 (A) |
| 1.45 | 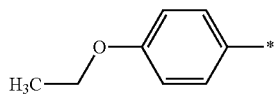 | *—CH₃ | II.1 | XI.2 | 385 [M + H]⁺ | 1.36 (A) |
| 1.46 | 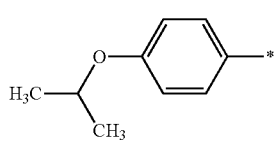 [SMILES: *c1ccc(OC(C)C)cc1] | *—CH₃ | II.6 | XI.2 | 399 [M + H]⁺ | 1.38 (A) |
| 1.47 | 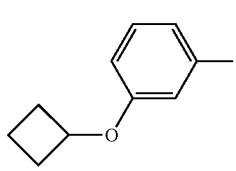 | *—CH₃ | II.7 | XI.2 | 411 [M + H]⁺ | 1.42 (A) |
| 1.48 | 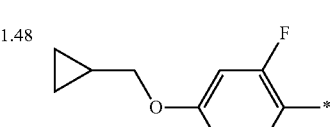 | *—CH₃ | II.2 | XI.2 | 429 [M + H]⁺ | 1.42 (A) |

The following compounds of general formula (I-4) are prepared analogously to Example 1.1, the educts used being shown in the column headed "E 1" and "E 2". Alternatively heating at reaction temperatures of 20-120° C. with or without microwave irradiation is used in the examples below:

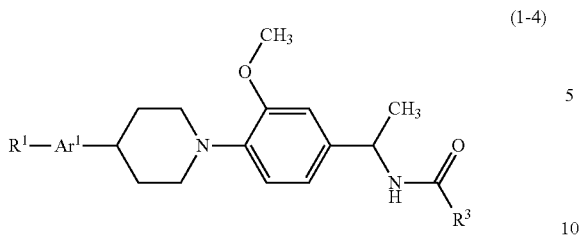

(1-4)

| Ex. | R$^1$—Ar$^1$ | R$^3$ | E 1 | E 2 | ESI-MS [m/z] | R$_t$ HPLC [min] (method) |
|---|---|---|---|---|---|---|
| 1.50 | H$_3$C–O–(CH$_3$-phenyl)–* | *—CH$_3$ | II.9 | XI.3 | 425 [M + H]$^+$ | 1.43 (A) |
| 1.51 | cyclobutyl-O-phenyl–* | *—CH$_3$ | II.8 | XI.3 | 423 [M + H]$^+$ | 1.42 (A) |
| 1.52 | H$_3$C–O–phenyl–* | *—CH$_3$ | II.3 | XI.3 | 411 [M + H]$^+$ | 1.41 (A) |

The following compounds of general formula (I-5) are prepared analogously to Example 1.1, the educts used being shown in the column headed "E 1" and "E 2". Alternatively heating at reaction temperatures of 20-120° C. with or without microwave irradiation is used in the examples below and BINAP/toluene is used instead of 2-(di-tert-butylphosphino) biphenyl/dioxane in example 1.61:

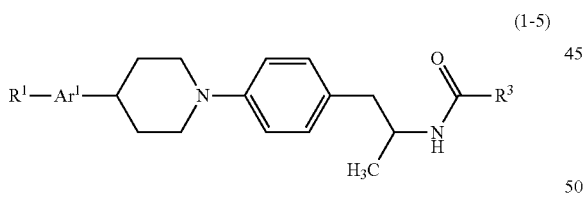

(1-5)

| Ex. | R$^1$—Ar$^1$ | R$^3$ | E 1 | E 2 | ESI-MS [m/z] | R$_t$ HPLC [min] (method) |
|---|---|---|---|---|---|---|
| 1.60 | H$_3$C–O–phenyl–* | *—CH$_3$ | II.1 | III.2 | 381 [M + H]$^+$ | 2.20 (C) |
| 1.61 | H$_3$C–O–phenyl–* | *—CH$_3$ | 4-(4-methoxyphenyl)-piperidine | III.2 | 367 [M + H]$^+$ | 2.16 (G) |

The following compounds of general formula (I-6) are prepared analogously to Example 1.1, the educts used being shown in the column headed "E 1" and "E 2". Alternatively heating at reaction temperatures of 20-120° C. with or without microwave irradiation is used in the examples below:

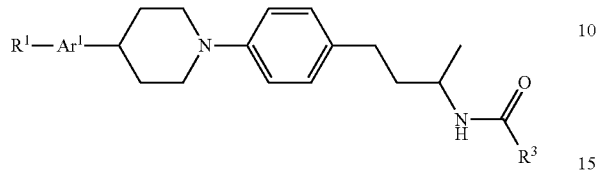

(I-6)

| Ex. | R¹—Ar¹ | R³ | E 1 | E 2 | ESI-MS [m/z] | $R_t$ HPLC [min] (method) |
|---|---|---|---|---|---|---|
| 1.70 | H₃C—O—⟨phenyl⟩—* | *—CH₃ | II.1 | III.4 | 395 [M + H]⁺ | 2.25 (C) |

Example 2

Example 2.1

(S)-1-Cyano-cyclopropanecarboxylic acid (1-{4-[4-(4-ethoxy-phenyl)-piperidin-1-yl]-phenyl}-ethyl)-amide

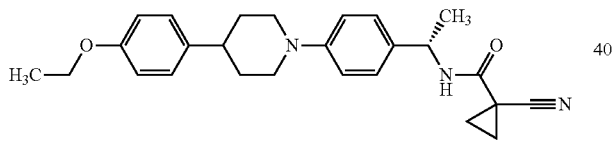

To a mixture of 14 mg (0.13 mmol) 1-cyano-cyclopropanecarboxylic acid in 1 mL DMF are added 52 μL (0.30 mmol) DIPEA and 49 mg (0.13 mmol) HATU. The mixture is stirred for 10 min at rt. Subsequently a mixture of 36 mg (0.10 mmol) (S)-1-{4-[4-(4-ethoxy-phenyl)-piperidin-1-yl]-phenyl}-ethylamine hydrochloride (XII.1) in 1 mL DMF is added and stirring is continued for 6 h at rt. The crude mixture is directly purified by HPLC (Sunfire, narrow gradients, water (+0.1% TFA)/methanol) to yield the desired product.

$C_{26}H_{31}N_3O_2$ (M=417.6 g/mol), ESI-MS: 418 [M+H]⁺

$R_t$ (HPLC): 1.92 min (method M)

The following compounds of general formula (2-1) are prepared analogously to Example 2.1, the educts used being shown in the column headed "E 1" and "E 2".

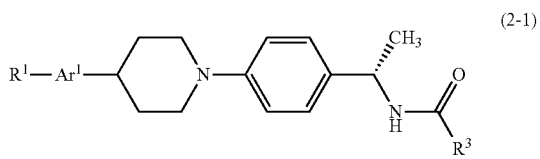

(2-1)

| Ex. | R¹—Ar¹ | R³ | E 1 | E 2 | ESI-MS [m/z] | $R_t$ HPLC [min] (method) |
|---|---|---|---|---|---|---|
| 2.1 | H₃C—O—⟨phenyl⟩—* | *—cyclopropyl-CN | XII.1 | HO-C(=O)-cyclopropyl-CN | 418 [M + H]⁺ | 1.92 (M) |
| 2.2 | H₃C—O—⟨phenyl⟩—* | *—thiazole | XII.1 | HO-C(=O)-thiazole | 436 [M + H]⁺ | 1.88 (M) |

-continued

| Ex. | R¹—Ar¹ | R³ | E 1 | E 2 | ESI-MS [m/z] | $R_t$ HPLC [min] (method) |
|---|---|---|---|---|---|---|
| 2.3 | H₃C-CH₂-O-C₆H₄-* | *-CH₂-S-CH₃ | XII.1 | HO-C(O)-CH₂-S-CH₃ | 413 [M + H]⁺ | 1.90 (M) |
| 2.4 | H₃C-CH₂-O-C₆H₄-* | *-CH₂-CH₃ | XII.1 | HO-C(O)-CH₃ | 381 [M + H]⁺ | 1.88 (M) |
| 2.5 | H₃C-CH₂-O-C₆H₄-* | *-CH₂-O-CH₃ | XII.2 | HO-C(O)-CH₂-O-CH₃ | 397 [M + H]⁺ | 1.90 (M) |
| 2.6 | H₃C-CH₂-O-C₆H₄-* | *-CF₃ | XII.1 | HO-C(O)-CF₃ | 421 [M + H]⁺ | 1.93 (M) |
| 2.7 | H₃C-CH₂-O-C₆H₄-* | *-C(CH₃)(cyclopropyl) | XII.1 | HO-C(O)-C(CH₃)(cyclopropyl) | 407 [M + H]⁺ | 1.94 (M) |

Example 3

Example 3.1

(S)-2-Acetylamino-oxazole-4-carboxylic acid (1-{4-[4-(4-ethoxy-phenyl)-piperidin-1-yl]-phenyl}-ethyl)-amide

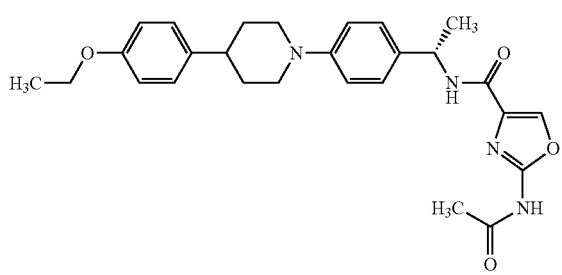 [SMILES: CCOc1ccc(C2CCN(c3ccc([C@H](C)NC(=O)c4coc(NC(C)=O)n4)cc3)CC2)cc1]

To a mixture of 2.0 mg (0.012 mmol) 2-acetylamino-oxazole-4-carboxylic acid, 3.6 mg (S)-1-{4-[4-(4-ethoxy-phenyl)-piperidin-1-yl]-phenyl}-ethylamine hydrochloride (XII.1) and 3.54 (0.02 mmol) DIPEA in 0.27 mL DMF are added 3.9 mg (0.012 mmol) TBTU. The mixture is shaken at rt for 12 h. 25 µl K₂CO₃ solution (3 M) is added, the mixture is filtered through basic alumina, washed with DMF/MeOH (9:1) and concentrated to yield the desired product.

$C_{27}H_{22}N_4O_4$ (M=476.6 g/mol), ESI-MS: 477 [M+H]⁺
$R_t$ (HPLC): 0.54 min (method O)

The following compounds of general formula (3-1) are prepared analogously to Example 3.1, the educts used being shown in the column headed "E 1" and "E 2".

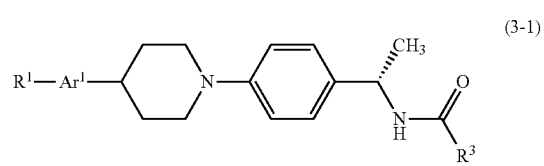

(3-1)

| Ex. | R¹—Ar¹ | R³ | E 1 | E 2 | ESI-MS [m/z] | R_t HPLC [min] (method) |
|---|---|---|---|---|---|---|
| 3.1 | 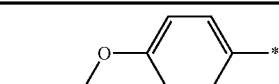 | 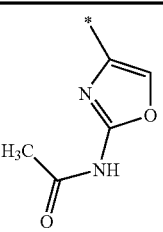 | XII.1 | 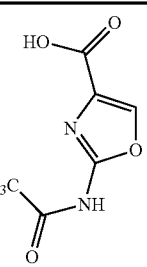 | 477 [M + H]⁺ | 0.54 (O) |
| 3.2 | 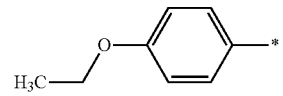 |  | XII.1 | 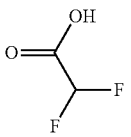 | 403 [M + H]⁺ | 0.53 (O) |
| 3.3 | 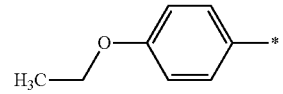 |  | XII.1 | 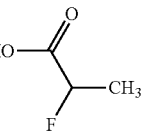 | 399 [M + H]⁺ | 0.55 (O) |
| 3.4 | 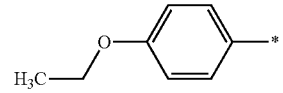 | 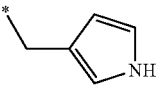 | XII.1 | 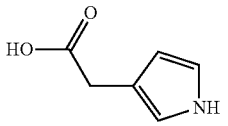 | 432 [M + H]⁺ | 0.55 (O) |
| 3.5 | 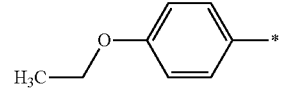 | 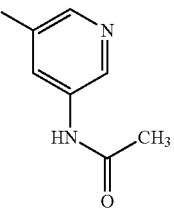 | XII.1 | 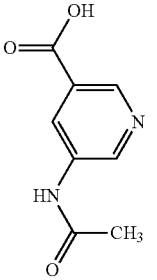 | 487 [M + H]⁺ | 0.54 (O) |
| 3.6 | 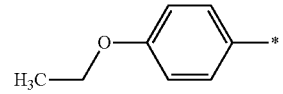 | 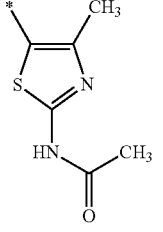 [SMILES: *c1sc(NC(C)=O)nc1C] | XII.1 | 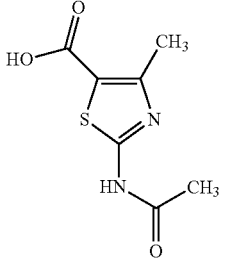 | 507 [M + H]⁺ | 0.54 (O) |
| 3.7 | 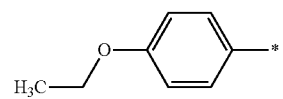 | 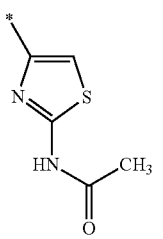 [SMILES: *c1csc(NC(C)=O)n1] | XII.1 | 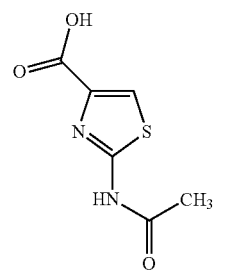 | 493 [M + H]⁺ | 0.54 (O) |

-continued

| Ex. | R¹—Ar¹ | R³ | E 1 | E 2 | ESI-MS [m/z] | $R_t$ HPLC [min] (method) |
|---|---|---|---|---|---|---|
| 3.8 | H₃C—O—⟨phenyl⟩—* | *—CH₂—F | XII.1 | HO—C(=O)—CH₂—F | 385 [M + H]⁺ | 0.54 (O) |
| 3.9 | H₃C—O—⟨phenyl⟩—* | *—CH₂—OH | XII.1 | HO—C(=O)—CH₂—OH | 383 [M + H]⁺ | 0.53 (O) |

Example 4

Example 4.1

(S)-3-(1-{4-[4-(4-Ethoxy-phenyl)-piperidin-1-yl]-phenyl}-ethyl)-1-ethyl-1-methyl-urea

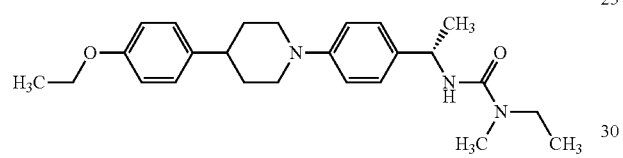

To 36 mg (0.10 mmol) (S)-1-{4-[4-(4-ethoxy-phenyl)-piperidin-1-yl]-phenyl}-ethylamine hydrochloride (XII.1) in 1.5 mL 1,4-dioxane are added 37 μL (0.25 mmol) DBU and 33 mg (0.20 mmol) CDT. The mixture is stirred for 5 min at rt. Subsequently 7.1 mg (0.12 mmol) ethyl-methyl-amine in 1.0 mL 1,4-dioxane are added and stirring is continued for 12 h at rt. The solvent is removed under reduced pressure, the residue is taken up in DMF and purified by HPLC (Sunfire, narrow gradients, water (+0.1% TFA)/methanol) to yield the desired product.

$C_{27}H_{22}N_4O_4$ (M=409.6 g/mol), ESI-MS: 410 [M+H]⁺

$R_t$ (HPLC): 1.36 min (method P)

The following compounds of general formula (4-1) are prepared analogously to Example 4.1, the educts used being shown in the column headed "E 1" and "E 2".

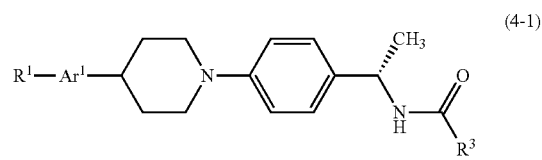

(4-1)

| Ex. | R¹—Ar¹ | R³ | E 1 | E 2 | ESI-MS [m/z] | $R_t$ HPLC [min] (method) |
|---|---|---|---|---|---|---|
| 4.1 | H₃C—O—⟨phenyl⟩—* | *—N(CH₃)(CH₂CH₃) | XII.1 | H—N(CH₃)(CH₂CH₃) | 410 [M + H]⁺ | 1.36 (P) |
| 4.2 | H₃C—O—⟨phenyl⟩—* | *—N(CH₃)(3-pyridyl) | XII.1 | HN(CH₃)(3-pyridyl) | 459 [M + H]⁺ | 1.15 (P) |
| 4.3 | H₃C—O—⟨phenyl⟩—* | *—morpholino | XII.1 | HN-morpholine | 438 [M + H]⁺ | 1.30 (P) |
| 4.4 | H₃C—O—⟨phenyl⟩—* | *—N(CH₂CH₃)(CH₂CH₂CH₃) | XII.1 | H—N(CH₂CH₃)(CH₂CH₂CH₃) | 424 [M + H]⁺ | 1.41 (P) |

Example 5

Example 5.1

(S)-(1-{4-[4-(4-Ethoxy-phenyl)-piperidin-1-yl]-phenyl}-ethyl)-carbamic acid methyl ester

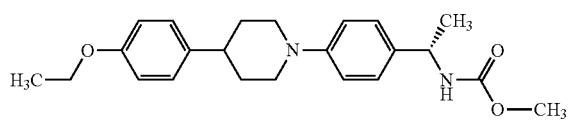

To a mixture of 36.1 mg (0.10 mmol) (S)-1-{4-[4-(4-ethoxy-phenyl)-piperidin-1-yl]-phenyl}-ethylamine hydrochloride (XII.1) and 42.7 µL (0.250 mmol) DIPEA in 2 mL THF are added 11.64 (0.150 mmol) methyl chloroformate at 0° C. The mixture is stirred for 12 h at rt. The solvent is removed under reduced pressure, the residue is taken up in DMF and purified by HPLC (Sunfire, narrow gradients, water (+0.1% TFA)/methanol) to yield the desired product.

$C_{23}H_{30}N_2O_3$ (M=382.5 g/mol), ESI-MS: 383 [M+H]$^+$
$R_t$ (HPLC): 1.52 min (method R)

Example 6

Example 6.1

(S)—N-(1-{4-[4-(4-Ethoxy-phenyl)-piperidin-1-yl]-phenyl}-ethyl)-N-methyl-acetamide

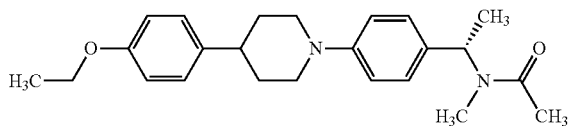 [SMILES: CCOc1ccc(C2CCN(c3ccc([C@H](C)N(C)C(C)=O)cc3)CC2)cc1]

To 34.5 mg (1.36 mmol, 95%) NaH in 2.5 mL THF at 0° C. are added 50.0 mg (0.136 mmol) of Example 1.2. The mixture is stirred for 10 min at 0° C. before 17.1 µL (0.273 mmol) methyl iodide are added and the mixture is stirred at rt for 2 h. The reaction is quenched by the addition of water and a sat. aq. NH$_4$Cl solution. The resulting mixture is extracted with DCM, the organic layers are combined and dried over MgSO$_4$. The solvent is removed in vacuo and the residue is triturated with diethyl ether.

$C_{24}H_{32}N_2O_2$ (M=380.5 g/mol), ESI-MS: 381 [M+H]$^+$
$R_t$ (HPLC): 2.16 min (method B)

The invention claimed is:

1. A compound of the formula I

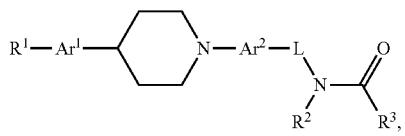

(I)

wherein
Ar$^1$ is selected from the group consisting of:

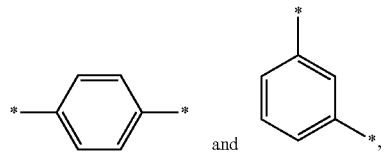

and, wherein the beforementioned phenylene group is optionally substituted with F, —CH$_3$ or —OCH$_3$;
Ar$^2$ is phenylene optionally substituted with F or —OCH$_3$;
L is selected from the group consisting of:
  straight-chain C$_{1-4}$-alkylene, which may optionally be substituted with one or two C$_{1-3}$-alkyl groups;
R$^1$ is selected from the group consisting of:
  C$_{1-4}$-alkyl-O—, C$_{3-4}$-cycloalkyl-O— and C$_{3-4}$-cycloalkyl-CH$_2$—O—,
    wherein each alkyl and cycloalkyl may be optionally substituted with one or two F atoms;
R$^2$ is selected from the group consisting of: H and C$_{1-3}$-alkyl; and
R$^3$ is selected from the group consisting of:
  C$_{1-3}$-alkyl, —O—(C$_{1-2}$-alkyl), C$_{3-5}$-cycloalkyl, R$^{N1}$R$^{N2}$N—, morpholinyl, heteroaryl and heteroaryl-CH$_2$—,
    wherein each alkyl may be optionally substituted with one to three F atoms or one CN, OH, —O—CH$_3$ and —S—CH$_3$, and
    wherein each cycloalkyl may be optionally substituted with one CN, OH, or —CH$_3$, and
    wherein each heteroaryl group is selected from the group consisting of pyrrolyl, imidazolyl, pyrazolyl, oxazoly, thiazolyl, benzimidazolyl and pyridinyl, and
    wherein each heteroaryl group may be optionally substituted with one or more substituents independently selected from the group consisting of phenyl, —CH$_3$ and —NH—C(=O)—CH$_3$, and
    wherein R$^{N1}$ is selected from the group consisting of H and C$_{1-3}$-alkyl, and
    wherein R$^{N2}$ is selected from the group consisting of H, C$_{1-3}$-alkyl and pyridinyl;
or a tautomer or pharmaceutically acceptable salt thereof.

2. A compound according to claim 1, wherein
Ar$^2$ is selected from the group consisting of:

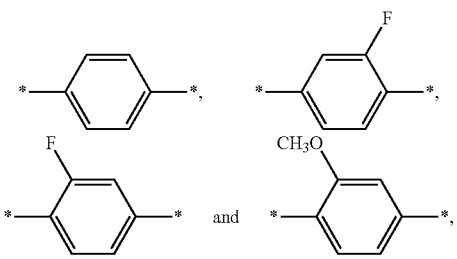

and, wherein the asterisk to the left side of each group indicates the bond which is connected to the piperidine ring of the core structure of the formula (I), and the asterisk to the right side of each group indicates the bond which is connected to L.

3. A compound according to claim 1, wherein
group L is selected from the group consisting of:
straight-chain $C_{1-3}$-alkylene, which may optionally be substituted with one methyl group.
4. A compound according to claim 3, wherein
L is —CH(CH$_3$)—.
5. A compound according to claim 1, wherein
$R^2$ is H or CH$_3$.
6. A compound according to claim 5, wherein
$R^2$ is H.
7. A compound according to claim 1, wherein
$R^1$ is selected from the group consisting of:
$C_{1-4}$-alkyl-O—, $C_{3-6}$-cycloalkyl-O— and $C_{3-6}$-cycloalkyl-$C_{1-3}$-alkyl-O—,
wherein each alkyl and cycloalkyl may be optionally substituted with one or more F atoms.
8. A compound according to claim 1, wherein
$R^3$ is selected from the group consisting of:
$C_{1-3}$-alkyl, —O—CH$_3$, cyclopropyl, $R^{N1}R^{N2}N$—, morpholinyl, heteroaryl and heteroaryl-CH$_2$—,
wherein each alkyl may be optionally substituted with one to three F atoms or one CN, OH, —O—CH$_3$ and —S—CH$_3$, and
wherein each cycloalkyl may be optionally substituted with one CN, or —CH$_3$, and
wherein each heteroaryl group is selected from the group consisting of pyrrolyl, pyrazolyl, oxazolyl, thiazolyl and pyridinyl, and
wherein each heteroaryl group may be optionally substituted with one or two substituents independently selected from the group consisting of —CH$_3$ and —NH—C(=O)—CH$_3$, and
wherein $R^{N1}$ is selected from the group consisting of H and $C_{1-2}$-alkyl, and
wherein $R^{N2}$ is selected from the group consisting of H, $C_{1-3}$-alkyl and pyridinyl.
9. A compound according to claim 8, wherein
$R^3$ is selected from the group consisting of:
$C_{1-3}$-alkyl, —CH$_2$F, —CHF$_2$, —CF$_3$, —CHF—CH$_3$, —CH$_2$—OH, —CH$_2$—OCH$_3$, —CH$_2$—S—CH$_3$, —OCH$_3$, —N(C$_{1-2}$-alkyl)$_2$,

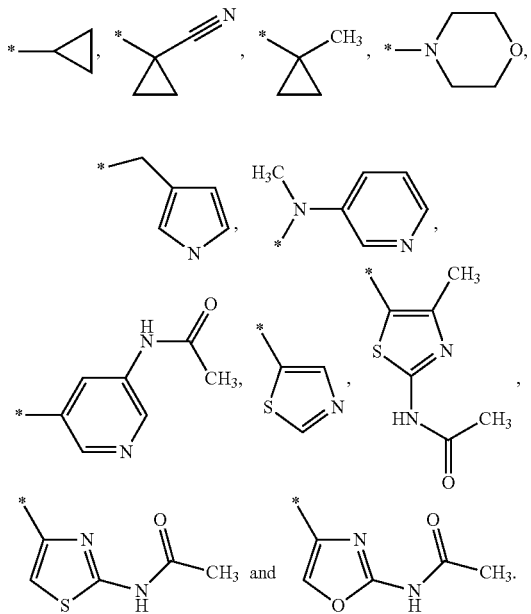

10. A compound according to claim 9, wherein
$R^3$ is selected from the group consisting of: —CH$_3$, cyclopropyl and —N(CH$_3$)$_2$.
11. A pharmaceutical composition comprising a compound according to claim 1 and a pharmaceutically acceptable carrier or diluent.
12. A method of treating obesity or dyslipidemia in a patient suffering from one of said conditions, which method comprises administering to said patient a therapeutically effective amount of a compound according to claim 1.
13. A compound according to claim 1, wherein
$Ar^2$ is selected from the group consisting of:

wherein the asterisk to the left side of each group indicates the bond which is connected to the piperidine ring of the core structure of the formula (I), and the asterisk to the right side of each group indicates the bond which is connected to L;
L is selected from the group consisting of:

$R^1$ is selected from the group consisting of:
$C_{1-4}$-alkyl-O—, $C_{3-4}$-cycloalkyl-O— and $C_{3-4}$-cycloalkyl-CH$_2$—O—,
wherein each alkyl or cycloalkyl may be optionally substituted with one to three F atoms;
$R^2$ is selected from the group consisting of: H; and
$R^3$ is selected from the group consisting of:
$C_{1-3}$-alkyl, —O—CH$_3$, cyclopropyl, $R^{N1}R^{N2}N$—, morpholinyl, heteroaryl and heteroaryl-CH$_2$—,
wherein each alkyl may be optionally substituted with one to three F atoms or one CN, OH, —O—CH$_3$ and —S—CH$_3$, and
wherein each cycloalkyl may be optionally substituted with one CN, or —CH$_3$, and
wherein each heteroaryl group is selected from the group consisting of pyrrolyl, pyrazolyl, oxazoly, thiazolyl and pyridinyl, and
wherein each heteroaryl group may be optionally substituted with one or two substituents independently selected from the group consisting of —CH$_3$ and —NH—C(=O)—CH$_3$, and
wherein $R^{N1}$ is selected from the group consisting of H and $C_{1-2}$-alkyl, and
wherein $R^{N2}$ is selected from the group consisting of H, $C_{1-3}$-alkyl and pyridinyl;
or a tautomer or pharmaceutically acceptable salt thereof.
14. A compound according to claim 13, wherein
$R^3$ is selected from the group consisting of:
—CH$_3$, cyclopropyl and —N(CH$_3$)$_2$.

15. A compounds according to claim 14, wherein Ar¹ and Ar² are each
.
16. A compound selected from the group consisting of:
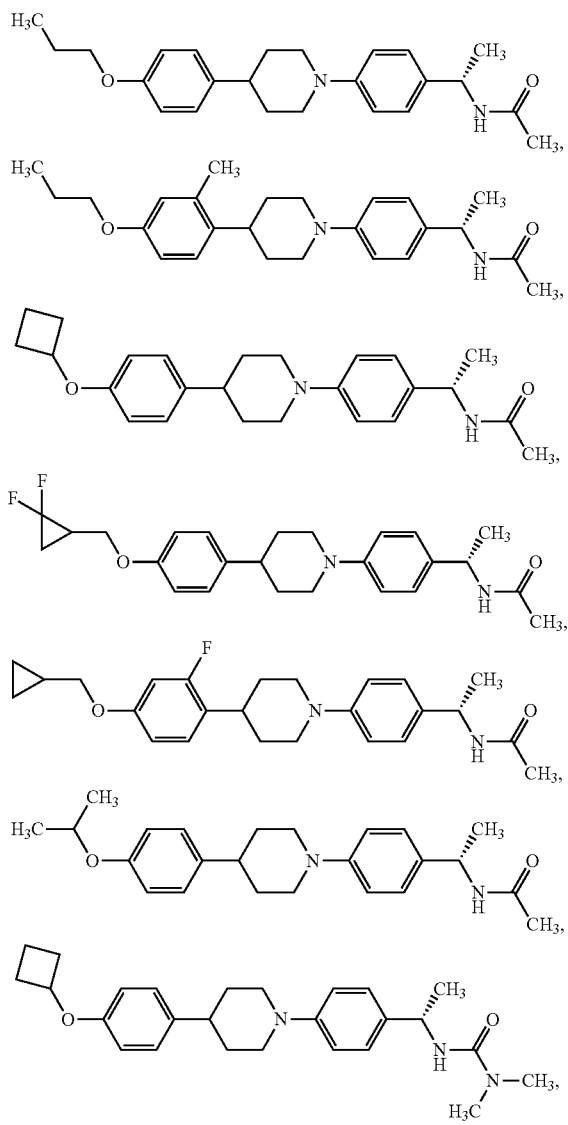
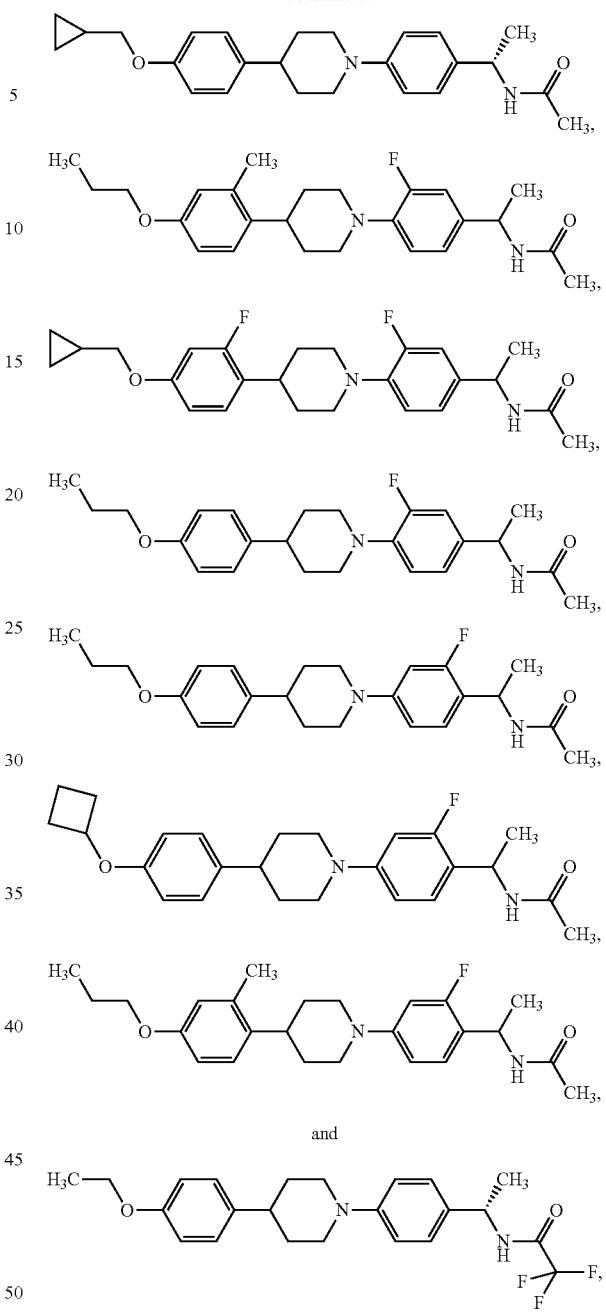
or a pharmaceutically acceptable salt thereof.
* * * * *